（12）United States Patent
Hannaford et al.

(10) Patent No.: US 12,357,404 B2
(45) Date of Patent: *Jul. 15, 2025

(54) SYSTEMS AND METHODS FOR BIFURCATED NAVIGATION CONTROL OF A MANIPULATOR CART INCLUDED WITHIN A COMPUTER-ASSISTED MEDICAL SYSTEM

(71) Applicant: Intuitive Surgical Operations, Inc., Sunnyvale, CA (US)

(72) Inventors: Sophia R. Hannaford, Oakland, CA (US); Marisa C. Babb, Santa Clara, CA (US); Simon P. DiMaio, San Carlos, CA (US); Craig Gotsill, San Francisco, CA (US); Omid Mohareri, San Francisco, CA (US); Dinesh Rabindran, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/646,127

(22) Filed: Apr. 25, 2024

(65) Prior Publication Data
US 2024/0277430 A1 Aug. 22, 2024

Related U.S. Application Data

(63) Continuation of application No. 17/610,348, filed as application No. PCT/US2020/035229 on May 29, 2020, now Pat. No. 11,992,281.
(Continued)

(51) Int. Cl.
*A61B 34/32* (2016.01)
*A61B 34/00* (2016.01)
(Continued)

(52) U.S. Cl.
CPC ............ *A61B 34/32* (2016.02); *A61B 34/25* (2016.02); *A61B 34/37* (2016.02); *A61B 34/70* (2016.02);
(Continued)

(58) Field of Classification Search
CPC ......... A61B 34/32; A61B 34/25; A61B 34/37; A61B 34/70; A61B 50/13; G05D 1/692; B25J 5/007; B25J 9/0084
See application file for complete search history.

(56) References Cited

U.S. PATENT DOCUMENTS 10,098,597 B2 10/2018 Schmidt
10,610,190 B2 4/2020 Hsieh
(Continued)

FOREIGN PATENT DOCUMENTS

CN 102232836 A 11/2011
CN 105912032 A 8/2016
(Continued)

OTHER PUBLICATIONS

International Preliminary Report on Patentability for Application No. PCT/US2020/035229 mailed on Dec. 9, 2021, 15 pages.
(Continued)

*Primary Examiner* — Peter D Nolan
*Assistant Examiner* — Mikko Okechukwu Obioha

(57) ABSTRACT

A system is configured to direct a manipulator cart to navigate, in a first bifurcated navigation control mode, from an initial location to an intermediate location; and direct the manipulator cart to navigate, in a second bifurcated navigation control mode, from the intermediate location to a target location. In the first bifurcated navigation control mode, the system is configured to autonomously control a steering of the manipulator cart while allowing operator control of a propulsion of the manipulator cart using a primary control
(Continued)

interface configured to facilitate operator control of both steering and propulsion of the manipulator cart. In the second bifurcated navigation control mode, the system is configured to autonomously control the steering of the manipulator cart while allowing operator control of the propulsion of the manipulator cart using a secondary control interface configured to facilitate operator control of the propulsion and not the steering of the manipulator cart.

20 Claims, 12 Drawing Sheets

Related U.S. Application Data

(60) Provisional application No. 62/855,558, filed on May 31, 2019.

(51) Int. Cl.
   *A61B 34/37* (2016.01)
   *A61B 50/13* (2016.01)
   *B25J 5/00* (2006.01)
   *B25J 9/00* (2006.01)
   *G05D 1/00* (2024.01)
   *G05D 1/692* (2024.01)

(52) U.S. Cl.
   CPC .............. *A61B 50/13* (2016.02); *B25J 5/007* (2013.01); *B25J 9/0084* (2013.01); *G05D 1/0027* (2013.01); *G05D 1/692* (2024.01)

(56) References Cited

U.S. PATENT DOCUMENTS

| | | | |
|---|---|---|---|
| 11,619,944 B2 | 4/2023 | Grossman et al. | |
| 2016/0311116 A1* | 10/2016 | Hill | B25J 9/1666 |
| 2018/0110494 A1* | 4/2018 | Hsieh | A61B 6/4405 |
| 2018/0353253 A1* | 12/2018 | Bowling | A61B 34/30 |
| 2021/0153958 A1* | 5/2021 | Meglan | A61B 34/35 |
| 2022/0241038 A1 | 8/2022 | Hannaford et al. | |
| 2022/0413511 A1* | 12/2022 | Yang | B25J 9/08 |

FOREIGN PATENT DOCUMENTS

| | | |
|---|---|---|
| CN | 107981884 A | 5/2018 |
| DE | 102016201701 A1 | 8/2016 |
| EP | 2815951 A2 | 12/2014 |
| EP | 2380496 B1 | 10/2017 |
| WO | WO-2007041295 A2 | 4/2007 |
| WO | WO-2019204013 A1 | 10/2019 |

OTHER PUBLICATIONS

International Search Report and Written Opinion for Application No. PCT/US2020/035229, mailed on Sep. 17, 2020,19 pages.
Office Action for Chinese Application No. CN20208021708, mailed Feb. 20, 2024, 23 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR BIFURCATED NAVIGATION CONTROL OF A MANIPULATOR CART INCLUDED WITHIN A COMPUTER-ASSISTED MEDICAL SYSTEM

RELATED APPLICATIONS

The present application is a continuation of U.S. patent application Ser. No. 17/610,348, filed Nov. 10, 2021, which is a U.S. National Stage Application under 35 U.S.C. § 371 of International Application No. PCT/US2020/035229, filed May 29, 2020, which claims priority to U.S. Provisional Patent Application No. 62/855,558, filed May 31, 2019, each of which is hereby incorporated by reference in its entirety.

BACKGROUND INFORMATION

Medical operations, such as various types of surgical and non-surgical procedures, may be performed using computer-assisted medical systems. In some examples, such computer-assisted medical systems may include a manipulator cart having one or more arms (e.g., robotic arms) configured for manipulating instruments used to carry out the medical operation. For instance, a manipulator cart may be positioned in proximity to a body being operated upon (e.g., a body of a patient, cadaver, training fixture, animal, or the like), and various types of medical operations may be performed on the body by way of the arms of the manipulator cart as directed by a medical practitioner (e.g., a clinician such as a surgeon, etc.) who is located at a control console that may be outside of the operational area. In this way, highly effective medical operations may be performed.

In preparation for such computer-assisted medical operations, a manipulator cart is typically navigated by a human operator from an initial location (e.g., a location where the manipulator cart has been kept when not in use and/or where the manipulator cart is draped and otherwise prepared for the operation) to a target location proximate to an operating table upon which the body is located that is to be operated upon. Unfortunately, however, various challenges (e.g., poor visibility afforded to the operator, obstacles on the path, narrow parameters characterizing the target location and target configuration of the manipulator cart, etc.) may make it difficult for the operator to effectively navigate the manipulator cart in an efficient manner.

SUMMARY

Systems and methods for bifurcated navigation control of a manipulator cart included within a computer-assisted medical system are described herein. For instance, one embodiment is implemented as a system comprising a memory storing instructions and a processor communicatively coupled to the memory and configured to execute the instructions. For example, the instructions may direct the processor to define a path whereby a manipulator cart included within a computer-assisted medical system is to navigate from an initial location to a target location. The instructions may also direct the manipulator cart to navigate, in a first bifurcated navigation control mode, along at least part of a first portion of the path extending from the initial location to an intermediate location on the path between the initial location and the target location. Additionally, the instructions may further direct the manipulator cart to navigate, in a second bifurcated navigation control mode, along at least part of a second portion of the path extending from the intermediate location to the target location. In the first bifurcated navigation control mode, the processor may autonomously control a steering of the manipulator cart while allowing operator control of a propulsion of the manipulator cart using a primary control interface configured to facilitate operator control of both steering and propulsion of the manipulator cart. In the second bifurcated navigation control mode, the processor also may autonomously control the steering of the manipulator cart while allowing operator control of the propulsion of the manipulator cart. However, in the second bifurcated navigation control mode, the operator control may be performed using a secondary control interface configured to facilitate operator control of the propulsion and not the steering of the manipulator cart.

Another exemplary embodiment is implemented as a method performed by a bifurcated navigation control system. For example, the method includes defining a path whereby a manipulator cart included within a computer-assisted medical system is to navigate from an initial location to a target location. The method further includes directing the manipulator cart to navigate, in a first bifurcated navigation control mode, along at least part of a first portion of the path extending from the initial location to an intermediate location on the path between the initial location and the target location; and directing the manipulator cart to navigate, in a second bifurcated navigation control mode, along at least part of a second portion of the path extending from the intermediate location to the target location. When portions of the method are performed in the first bifurcated navigation control mode, the bifurcated navigation control system may autonomously control a steering of the manipulator cart while allowing operator control of a propulsion of the manipulator cart using a primary control interface configured to facilitate operator control of both steering and propulsion of the manipulator cart. Additionally, when portions of the method are performed in the second bifurcated navigation control mode, the bifurcated navigation control system may autonomously control the steering of the manipulator cart while allowing operator control of the propulsion of the manipulator cart using a secondary control interface configured to facilitate operator control of the propulsion and not the steering of the manipulator cart.

Yet another exemplary embodiment is implemented by a non-transitory, computer-readable medium storing instructions that, when executed, direct a processor of a computing device to perform operations described herein. For instance, the instructions may direct the processor to define a path whereby a manipulator cart included within a computer-assisted medical system is to navigate from an initial location to a target location. The instructions may also direct the manipulator cart to navigate, in a first bifurcated navigation control mode, along at least part of a first portion of the path extending from the initial location to an intermediate location on the path between the initial location and the target location; as well as to navigate, in a second bifurcated navigation control mode, along at least part of a second portion of the path extending from the intermediate location to the target location. In the exemplary first bifurcated navigation control mode, the instructions may direct the processor to autonomously control a steering of the manipulator cart while allowing operator control of a propulsion of the manipulator cart using a primary control interface configured to facilitate operator control of both steering and propulsion of the manipulator cart. In the exemplary second bifurcated navigation control mode, the instructions may direct the processor to autonomously control the steering of the manipulator cart while allowing operator control of the propulsion of the manipulator cart using a secondary control interface configured to facilitate operator control of the propulsion and not the steering of the manipulator cart.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
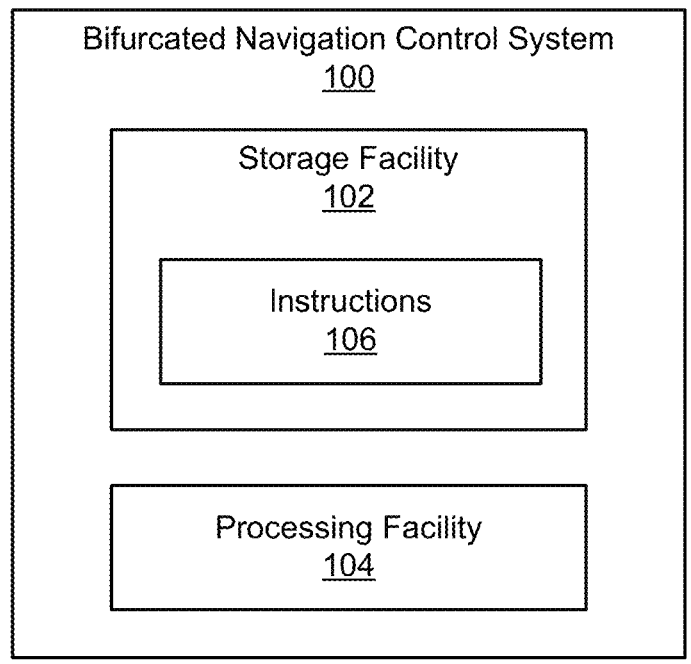
FIG. 1 illustrates an exemplary bifurcated navigation control system for bifurcated navigation control of a manipulator cart included within a computer-assisted medical system according to principles described herein.

Systems and methods for bifurcated navigation control of a manipulator cart included within a computer-assisted medical system are described herein. For example, in order to facilitate use of a manipulator cart to perform an operation, systems and methods described herein provide bifurcated navigation control modes that automatically assist an operator in navigating a manipulator cart from an initial location (e.g., a storage location) to a target location (e.g., a location at which the manipulator cart is ready for use in performing the operation). Systems and methods described herein also provide bifurcated navigation control modes that automatically assist an operator in navigating a manipulator cart from an initial orientation and/or configuration (e.g. a stowed configuration) to a target orientation and/or configuration (e.g. an orientation and/or a configuration at which the manipulator cart is ready for use in performing the operation). Examples of an operation that may be performed using an implementation of the manipulator carts described herein include medical procedures such as minimally invasive surgical or non-surgical procedures performed by way of an artificial or natural orifice in a body of a live human patient or another suitable body that may be living or non-living, biological or non-biological, natural or artificial, or the like (e.g., including but not limited to a body of an animal, of a cadaver, of a training fixture, etc.).

In a bifurcated navigation control mode, a processor autonomously controls a steering of the manipulator cart while allowing operator control of a propulsion of the manipulator cart using a control interface. For example, the operator may direct the manipulator cart forward and backward at a speed comfortable for the operator while the manipulator cart is autonomously steered along an appropriate path. In some examples, different bifurcated navigation control modes associated with different control interfaces may be provided to further facilitate navigation of a manipulator cart to a target destination and/or configuration.

In one implementation, for instance, a bifurcated navigation control system may include or be implemented by a memory storing instructions and a processor communicatively coupled to the memory and configured to execute the instructions to 1) define a path whereby a manipulator cart included within a computer-assisted medical system is to navigate from an initial location to a target location, 2) direct the manipulator cart to navigate, in a first bifurcated navigation control mode, along at least part of a first portion of the path extending from the initial location to an intermediate location on the path between the initial location and the target location, and 3) direct the manipulator cart to navigate, in a second bifurcated navigation control mode, along at least part of a second portion of the path extending from the intermediate location to the target location.

In both the first and second bifurcated navigation control modes, the processor may autonomously control a steering of the manipulator cart while allowing operator control of a propulsion of the manipulator cart. However, in the first bifurcated navigation control mode, the processor may allow the operator control of the propulsion using a primary control interface configured to facilitate operator control of both steering and propulsion of the manipulator cart (e.g., a standard control interface such as a handlebar-based control interface integrated into the manipulator cart), while in the second bifurcated navigation control mode, the processor may allow the operator control of the propulsion using a secondary control interface distinct and separate from the primary control interface, and configured to facilitate operator control of the propulsion and not the steering of the manipulator cart (e.g., an alternative control interface based on external stimulus applied to an arm of the manipulator cart, gesture-based commands, voice commands, a separate input device such as a separate joystick or control pad or the like). In this way, one operator may direct navigation of the manipulator cart from different places as may be convenient (e.g., behind the cart and in front of the cart at different times during the navigation), or multiple operators (e.g., one "sterile" operator who has scrubbed in and is allowed to be in a sterile field associated with the medical operation, and one "non-sterile" operator who has not scrubbed in and is not allowed to be in the sterile field) may cooperate to direct the navigation of the manipulator cart in other situations.

Aspects of the bifurcated navigation control systems and methods described herein primarily relate to implementations employing a computer-assisted medical system such as a minimally invasive surgical system. As will be described in more detail below, however, it will be understood that inventive aspects disclosed herein may be embodied and implemented in various ways, including by employing robotic and non-robotic embodiments and implementations. Implementations relating to surgical or other medical systems are merely exemplary and are not to be considered as limiting the scope of the inventive aspects disclosed herein. For example, any reference to surgical instruments, surgical techniques, and/or other such details relating to a surgical context will be understood to be non-limiting as the instruments, systems, and methods described herein may be used for medical treatment or diagnosis, cosmetic improvements, imaging of human or animal anatomy, gathering data from human or animal anatomy, setting up or taking down systems, training medical or non-medical personnel, and so forth (any of which may or may not also involve surgical aspects). In other examples, the instruments, systems, and methods described herein may also be used for procedures performed on, or with, animals, human cadavers, animal cadavers, portions of human or animal anatomy, tissue removed from human or animal anatomies (which may or may not be re-implanted within the human or animal anatomy), non-tissue work pieces, training models, and so forth. In yet other examples, the instruments, systems, and methods described herein may be applied for non-medical purposes including for industrial systems, general robotics, teleoperational systems, and/or sensing or manipulating non-tissue work pieces.

Additionally, while certain examples described herein involve two separate bifurcated navigation control modes each associated with different control interfaces (e.g., the primary and the secondary control interfaces described herein), it will be understood that, in certain examples, a single bifurcated navigation control mode and a single control interface (e.g., either a primary or a secondary bifurcated navigation control mode) may be employed throughout the navigation of the manipulator cart.

Various benefits may be provided by the bifurcated navigation control systems and methods described herein. For example, navigation of a manipulator cart by way of a computer-assisted bifurcated navigation control mode such as those described herein may result in more effective and accurate positioning of the manipulator cart, in a safer manner with less risk of equipment damage, and in a more timely manner than when standard navigation control modes (i.e., navigation control modes in which an operator entirely directs both steering and propulsion of the manipulator cart) are employed. Different types of operations may require different cart placements in relation to the body to be operated upon, and, in certain examples, operators tasked with navigating the manipulator cart may not be intimately involved in certain aspects of the operation such that these operators may not fully understand the ideal target placement (e.g., target location, target orientation, target configuration, etc.) of the manipulator cart. Additionally, because every minute in a typical surgical operating room is costly, it is important that as little time as possible be lost in navigating a manipulator cart to its target location (and/or target orientation or target configuration, as applicable). As a result, conventional navigation of manipulator carts to the target location may suffer from either or both of suboptimal placement (e.g., a non-ideal or inaccurate final placement of the manipulator cart for a given operation type) and inefficient placement (e.g., an ideal or non-ideal placement that takes more time than is necessary to achieve). It is a significant benefit, therefore, that systems and methods described herein facilitate manipulator cart navigation in a manner that results in both optimal and efficient manipulator cart placement.

Another exemplary benefit of the systems and methods described herein is that a human operator retains propulsion control of the manipulator cart navigation even as the system autonomously handles the steering control. It may be impractical or otherwise undesirable for the navigation of a manipulator cart to be fully automated such that both steering and propulsion are autonomously controlled. For example, it may be desirable (e.g., for efficiency reasons, safety reasons, etc.) for one or more human operators to always be directly involved in the movement of a large, heavy, valuable piece of equipment such as a manipulator cart. Accordingly, by bifurcating the steering control of the manipulator cart to be performed autonomously by the system while maintaining the propulsion control of the manipulator cart as a task performed by a human operator, an effective and efficient navigation and positioning of the manipulator cart may be consistently achieved in a convenient, safe, and cost-effective way that is partially or entirely independent of the operator's specific knowledge of the ideal cart placement for a given operation type.

Yet another benefit arises from the use, described herein, of different bifurcated navigation control modes associated with different types of control interfaces (e.g., a primary control interface configured to facilitate operator control of both steering and propulsion of the manipulator cart versus a secondary control interface configured to facilitate operator control of the propulsion and not the steering of the manipulator cart). In some situations, for example, a non-sterile operator may direct the navigation of the manipulator cart from an initial location to an intermediate location at or near a boundary of a sterile field within which the operation is to be performed. This may represent the largest part the total path that is to be traversed by the manipulator cart, so the non-sterile operator may use the primary control interface so as to have the option to manually steer the manipulator cart along at least a portion of the path if appropriate (e.g., if the operator so chooses, if the bifurcated navigation control system requires assistance navigating around a particular obstacle or defining a particular portion of the path, etc.).

The final leg of the path between the intermediate location and the target location within the sterile field may be relatively short, but it may not be desirable for the non-sterile operator to direct the navigation of this final leg. Instead, another operator (e.g., a sterile operator who is allowed within the sterile field) may be in a better position to direct the manipulator cart to complete the last leg of the path by way of a secondary control interface that only allows the operator to control the propulsion while the system handles the steering control. For example, the secondary control interface may require the sterile operator to gently pull on an arm of the manipulator cart, to perform a particular hand gesture, to speak a particular voice command, or to otherwise indicate that the manipulator cart is to move forward on the predefined path the cart is configured to steer along. Then, once the manipulator cart arrives at a target location (and/or a target orientation or a target configuration, as applicable), the operation may be performed. An example target orientation and configuration for the manipulator cart is with the manipulator cart facing a target object with the manipulator arms positioned in a desirable way. An example target configuration for a kinematic structure of the manipulator cart is with one or more joints or links of the kinematic structure at target positions or orientations, or within a range of target positions or orientations, etc., for those joints or links. It will be understood that this specific example is provided only as one illustrative scenario and that, in other examples, the same operator and/or the same control interface may be employed for an entirety of the navigation of the manipulator cart along the path.

Various embodiments will now be described in more detail with reference to the figures. The systems and methods described herein may provide one or more of the benefits mentioned above as well as various additional and/or alternative benefits that will be made apparent by the description below.

FIG. 1 illustrates an exemplary bifurcated navigation control system 100 ("system 100") for bifurcated navigation control of a manipulator cart included within a computer-assisted medical system. As will be described and illustrated in more detail below, a "manipulator cart," as used herein, may refer to any robotic or other system that includes one or more manipulators (e.g., manipulator arms, etc.) configured to facilitate performance of an operation (e.g., a medical operation such as a surgical procedure, etc.), and that is configured to be independently navigable from one location to another, rather than being mounted, for example, on a physical track.

As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.).

In some examples, facilities 102 and 104 may be integrated into a single device (e.g., a manipulator cart control system, etc.), while, in other examples, facilities 102 and 104 may be distributed between multiple devices and/or multiple locations as may serve a particular implementation. For instance, in one implementation of system 100, the manipulator cart itself may include one or more built-in processors, data storage devices, sensors, communication interfaces, and so forth for implementing system 100. In contrast, in other implementations of system 100, some or all of these components may not be integrated into the manipulator cart itself but, rather, may be implemented on other computing systems as may serve a particular implementation (e.g., edge servers, cloud servers, computing devices integrated with other components of a computer-assisted medical system that includes the manipulator cart, etc.).

Storage facility 102 may maintain (e.g., store) executable data used by processing facility 104 to perform any of the functionality described herein. For example, storage facility 102 may store instructions 106 that may be executed by processing facility 104 to perform any of the functionality described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various processing functions associated with bifurcated navigation control of the manipulator cart. For example, processing facility 104 may define a path whereby the manipulator cart is to navigate from an initial location to a target location. Processing facility 104 may also direct the manipulator cart to navigate, in a first bifurcated navigation control mode, along at least part of a first portion of the path extending from the initial location to an intermediate location on the path between the initial location and the target location; and to navigate, in a second bifurcated navigation control mode, along at least part of a second portion of the path extending from the intermediate location to the target location. Analogously, in embodiments with target orientations and/or target configurations, processing facility 104 may also direct the manipulator cart, in a first bifurcated navigation control mode, from an initial orientation and/or initial configuration to a target orientation and/or target configuration along with guiding the manipulator cart from the initial location to the target location.

In both the first and second bifurcated navigation control modes, processing facility 104 may autonomously control a steering of the manipulator cart while allowing operator control of a propulsion of the manipulator cart using a control interface. As used herein, controlling the "steering" of a manipulator cart may refer to some or all aspects of navigation control that involve defining the direction in which motion vectors are directed (e.g., which way the wheels of the manipulator cart are pointing, etc.). For example, using a standard automobile as an analogy, the steering control of an automobile may relate to the control of the automobile imposed by way of the steering wheel. In contrast, controlling the "propulsion" of a manipulator cart may refer to some or all aspects of navigation control that involve defining the magnitude and/or sign (e.g., positive or negative) of the motion vectors (e.g., whether and to what degree the wheels of the manipulator cart are turning in either a forward or backward direction). For example, referring again to the automobile analogy, the propulsion control of the automobile may be performed by way of the gas pedal, the brake, and/or the gear shift (e.g., whether the automobile is in a "park" mode, a "drive" mode, a "reverse" mode, etc.).

While having the bifurcation of steering and propulsion control in common, the first and second bifurcated navigation control modes are distinct from one another in that the first bifurcated navigation control mode is configured to allow the operator control of the propulsion using a primary control interface, while the second bifurcated navigation control mode is configured to allow the operator control of the propulsion using a secondary control interface. As will be described in more detail below, the primary control interface may be a full or standard manipulator cart control interface configured to facilitate operator control of both steering and propulsion of the manipulator cart. In contrast, the secondary control interface may be an abbreviated or auxiliary control interface. For instance, in some examples, the secondary control interface may be configured to facilitate operator control of the propulsion but not the steering of the manipulator cart. In other examples, the secondary control interface may be configured to facilitate operator control of both the propulsion and the steering of the manipulator cart, but may be auxiliary to the primary control interface by otherwise including fewer features than the primary control interface, by being used from an opposite side of the manipulator cart than the primary control interface, or in other suitable ways. For example, the secondary control interface may be configured to be used by an operator in a sterile environment (e.g., an operator located in a sterile field on a patient side of the manipulator cart, rather than located in a non-sterile field on the opposite side of the manipulator cart).

Processing facility 104 may perform the functions described above and other functions described herein in any suitable manner, as will be described in more detail below.

In some implementations, system 100 (e.g., processing facility 104) may be configured to provide bifurcated navigation control of a manipulator cart in real time. As used herein, a function may be said to be performed in real time when the function relates to or is based on dynamic, time-sensitive information and the function is performed while the time-sensitive information remains accurate or otherwise relevant. Due to processing times, communication latency, and other inherent delays in physical systems, certain functions may be considered to be performed in real time when performed immediately and without undue delay, even if performed after small delay (e.g., a delay up to a few seconds or the like). As one example of real-time functionality, processing facility 104 may define a path based on the real-time states of obstacles in between the initial location and the target location, and may update the path as the state of obstacles changes. As another example of real-time functionality, in some embodiments where target orientations and/or configurations exist for the manipulator cart, processing facility 104 may define changes in cart orientation and/or configuration to achieve target orientations and/or configurations based on real-time states of obstacles.

System 100 may be used in various contexts with various different types of technologies as may serve a particular implementation. For example, system 100 may be used in a medical context such as in preparation for a computer-assisted medical procedure in which an operation is performed inside of any suitable type of body described herein. In other implementations, system 100 may be used in medical contexts that are not surgical in nature (e.g., diagnostic or exploratory imaging without surgical elements), or that are not for treatment or diagnosis (e.g., training or other procedures where such procedures do not involve treatment). Additionally, in certain implementations, system 100 may be used in non-medical contexts. For instance, system 100 may be useful for navigating other types of large, free-moving objects that may or may not fall under the category of a manipulator cart, as that term is used herein.

To illustrate an exemplary context in which system 100 may be implemented and employed, an exemplary computer-assisted medical system that implements system 100 and includes a manipulator cart will now be described. The computer-assisted medical system described below is illustrative and not limiting. It will be understood that bifurcated navigation control systems and methods described herein may operate as part of or in conjunction with the computer-assisted medical system described herein, with other suitable computer-assisted medical systems that may or may not be surgical systems, and/or with other suitable medical and/or non-medical systems as may serve a particular implementation.

Figure 2:
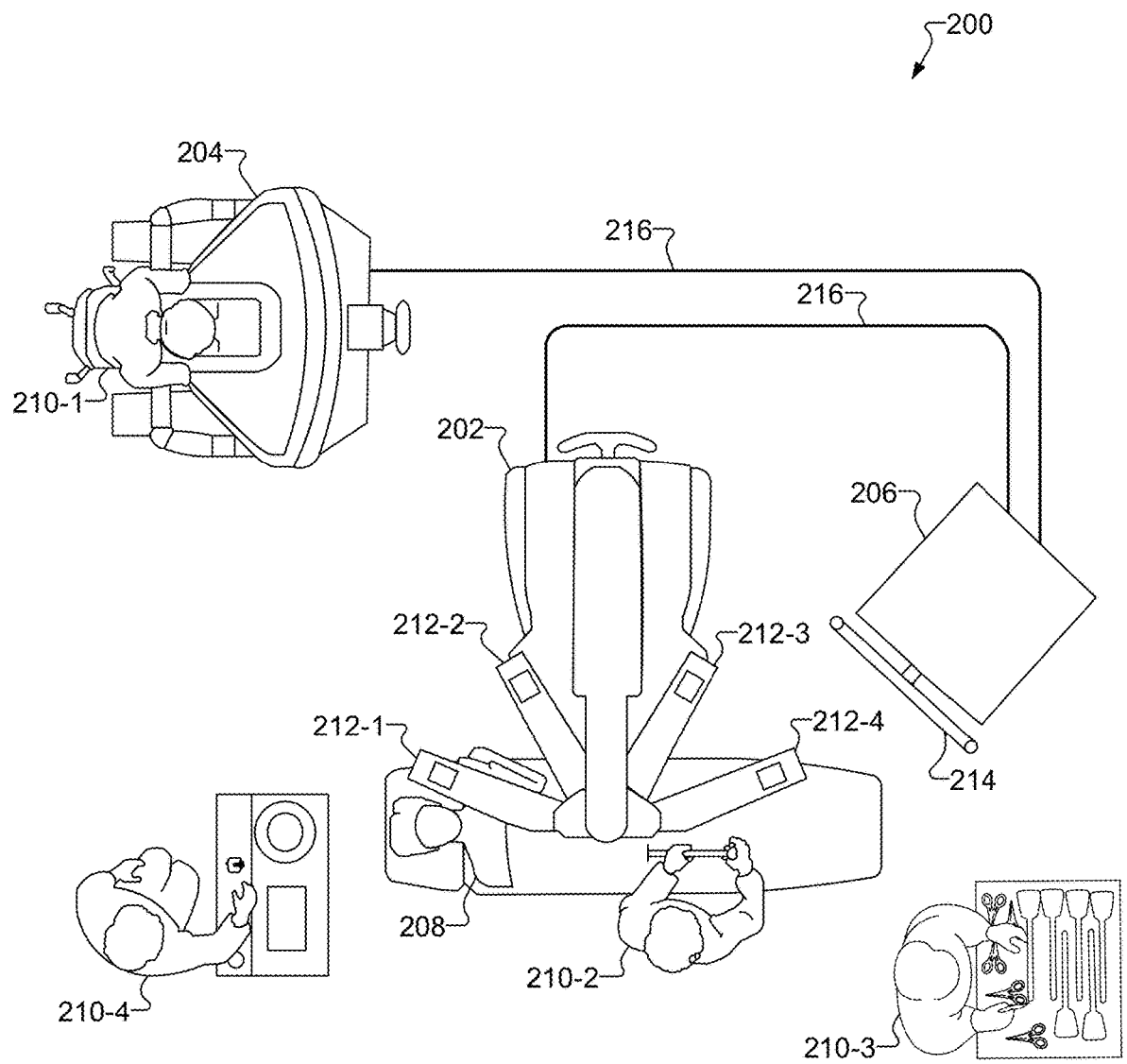
FIG. 2 illustrates an exemplary computer-assisted medical system according to principles described herein.

FIG. 2 illustrates an exemplary computer-assisted medical system 200 ("medical system 200") that may be used to perform surgical and/or non-surgical medical procedures. As shown, medical system 200 may include a manipulator cart 202, a user control system 204, and an auxiliary system 206 communicatively coupled one to another. Medical system 200 may be utilized by a medical team to perform a computer-assisted medical procedure or other such operation on a body of a patient 208 or on any other body as may serve a particular implementation. As shown, the medical team may include a first clinician 210-1 (such as a surgeon for a surgical procedure), an assistant 210-2, a nurse 210-3, and a second clinician 210-4 (such as an anesthesiologist for a surgical procedure), all of whom may be collectively referred to as "team members 210," and each of whom may control, interact with, or otherwise be a user of medical system 200. Additional, fewer, or alternative team members may be present during a medical procedure as may serve a particular implementation. For example, for some medical procedures, the "clinician 210-1" may not be a medical doctor. Further, team composition for non-medical procedures would generally be different and would include other combinations of members serving non-medical roles.

While FIG. 2 illustrates an ongoing minimally invasive medical procedure such as a minimally invasive surgical procedure, it will be understood that medical system 200 may also be used to perform open medical procedures or other types of operations that may benefit from the accuracy and convenience of medical system 200. For example, operations such as exploratory imaging operations, mock medical procedures used for training purposes, and/or other operations may also be performed using medical system 200.

As shown in FIG. 2, manipulator cart 202 may include a plurality of manipulator arms 212 (e.g., arms 212-1 through 212-4) to which a plurality of instruments (e.g., surgical instruments, other medical instruments, or other instruments) may be coupled. Each instrument may be implemented by any suitable surgical tool (e.g., a tool having tissue-interaction functions), medical tool, imaging device (e.g., an endoscope), sensing instrument (e.g., a force-sensing instrument), diagnostic instrument, or the like that may be used for a computer-assisted medical procedure such as a surgical procedure on patient 208 (e.g., by being at least partially inserted into patient 208 and manipulated to perform a computer-assisted medical procedure on patient 208). While manipulator cart 202 is depicted and described herein as including four manipulator arms 212, it will be recognized that manipulator cart 202 may include only a single manipulator arm 212 or any other number of manipulator arms as may serve a particular implementation. Additionally, it will be understood that, in some exemplary systems, certain instruments may not be coupled to or controlled by manipulator arms, but rather may be handheld and controlled manually (e.g., by a surgeon, other clinician, or other medical personnel). For instance, certain handheld devices of this type may be used in conjunction with or as an alternative to computer-assisted instrumentation that is coupled to manipulator arms 212 shown in FIG. 2.

Manipulator arms 212 and/or instruments attached to manipulator arms 212 may include one or more displacement transducers, orientational sensors, and/or positional sensors used to generate raw (i.e., uncorrected) kinematics information. One or more components of medical system 200 may be configured to use the kinematics information to track (e.g., determine positions of) and/or control the instruments.

During the medical operation, user control system 204 may be configured to facilitate control by clinician 210-1 of manipulator arms 212 and instruments attached to manipulator arms 212. For a surgical procedure, for example, clinician 210-1 may be a surgeon. Clinician 210-1 may interact with user control system 204 to remotely move or manipulate manipulator arms 212 and the instruments. To this end, user control system 204 may provide clinician 210-1 with imagery (e.g., high-definition 3D imagery) of an operational area associated with patient 208 as captured by an imaging device. In certain examples, user control system 204 may include a stereo viewer having two displays where stereoscopic images of an internal view of the body of patient 208 generated by a stereoscopic imaging device may be viewed by clinician 210-1. Clinician 210-1 may utilize the imagery to perform one or more procedures with one or more instruments attached to manipulator arms 212.

To facilitate control of instruments, user control system 204 may include a set of master controls. These master controls may be manipulated by clinician 210-1 to control movement of instruments (e.g., by utilizing robotic and/or teleoperation technology). The master controls may be configured to detect a wide variety of hand, wrist, and finger movements by clinician 210-1. In this manner, clinician 210-1 may intuitively perform a procedure using one or more instruments.

Auxiliary system 206 may include one or more computing devices configured to perform processing operations of medical system 200. In such configurations, the one or more computing devices included in auxiliary system 206 may control and/or coordinate operations performed by various other components of medical system 200 such as manipulator cart 202 and/or user control system 204. For example, a computing device included in user control system 204 may transmit instructions to manipulator cart 202 by way of the one or more computing devices included in auxiliary system 206. As another example, auxiliary system 206 may receive and process image data representative of imagery captured by an imaging device attached to one of manipulator arms 212.

In some examples, auxiliary system 206 may be configured to present visual content to team members 210 who may not have other access to the images provided to clinician 210-1 at user control system 204. To this end, auxiliary system 206 may include a display monitor 214 configured to display one or more user interfaces, one or more images (e.g., 2D images) of the operational area, information associated with patient 208 and/or the medical procedure, and/or any other content as may serve a particular implementation. In some examples, display monitor 214 may display images of an internal view of the operational area together with additional content (e.g., graphical content, contextual information, etc.). Display monitor 214 may be implemented by a touchscreen display with which team members 210 may interact (e.g., by way of touch gestures) to provide user input to medical system 200, or may be implemented by any other type of display screen as may serve a particular implementation.

As will be described in more detail below, system 100 may be implemented within or may operate in conjunction with medical system 200. For instance, in certain implementations, system 100 may be implemented entirely by manipulator cart 202, or by sensors and/or computing components implemented by one or more other components of medical system 200.

Manipulator cart 202, user control system 204, and auxiliary system 206 may be communicatively coupled one to another in any suitable manner. For example, as shown in FIG. 2, manipulator cart 202, user control system 204, and auxiliary system 206 may be communicatively coupled by way of control lines 216, which may represent any wired or wireless communication link as may serve a particular implementation. To this end, manipulator cart 202, user control system 204, and auxiliary system 206 may each include one or more wired or wireless communication interfaces, such as one or more local area network interfaces, Wi-Fi network interfaces, cellular interfaces, and so forth.

Figure 3:
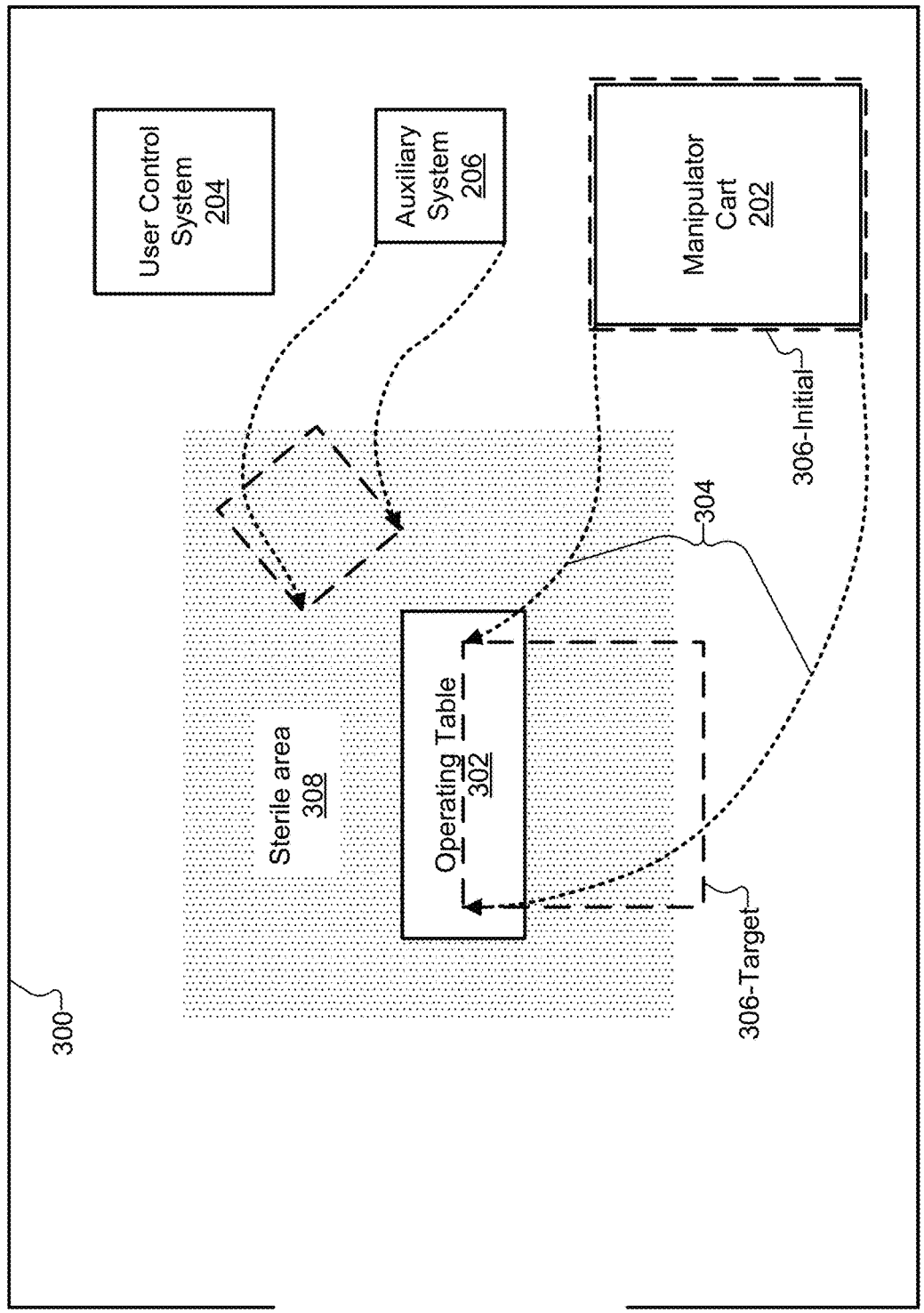
FIGS. 3 and 4 illustrate respective exemplary operating rooms within which an exemplary manipulator cart is to be navigated along an exemplary path from an initial location to a target location according to principles described herein.

To illustrate a specific environment and scenario in which system 100 may be employed to perform bifurcated navigation control of a manipulator cart such as manipulator cart 202, FIG. 3 shows an exemplary operating room 300 within which manipulator cart 202 is to be navigated toward an operating table 302 along an exemplary path 304 that extends from an initial location 306-initial to a target location 306-target. Operating room 300 provides an environment in which, under direction of one or more members of a medical operation team (e.g., team members 210), medical system 200 is configured to perform a medical operation on a body located on operating table 302.

FIG. 3 depicts a relatively small operating room 300 with a relatively simple layout. Specifically, as shown, location 306-initial is located relatively close to location 306-target within operating room 300, and there are not shown any obstacles between locations 306-initial and 306-target. As a result, path 304 is shown to be relatively straightforward as a path with a single gentle curve.

System 100 may define locations 306 (e.g., location 306-initial and 306-target), as well as other locations described herein, based on any suitable coordinate system or other formal or informal spatial characterization. For instance, a global coordinate system relative to operating table 302, a door or center of operating room 300, a storage location of manipulator cart 202, or any other suitable origin point may be defined, and locations 306 may be defined and analyzed with respect thereto.

As shown, location 306-initial may be a location that is tucked out of the way in a corner of operating room 300. For example, this location may be a storage location for manipulator cart 202 when medical system 200 is not in use (e.g., between medical operations, when a non-computer-assisted medical operation is being performed on operating table 302, etc.). Location 306-initial may also or alternatively be a preparation location for manipulator cart 202 where manipulator cart 202 may be covered with drapes and/or otherwise be sterilized and prepared to enter a sterile field 308 of operating room 300 in which the operation is to be performed.

Location 306-target may be a location that is relatively proximate to operating table 302. Specifically, location 306-target may be positioned where manipulator cart 202 is to be located during performance of the medical operation on the body, therefore making location 306-target nearer than location 306-initial to operating table 302. As depicted in FIG. 3, location 306-target may overlap with operating table 302 from the top view because arms 212 incorporated within manipulator cart 202 may hover over operating table 302 when manipulator cart 202 is in an operative position at operating table 302. In some examples, location 306-target may be specifically selected by an operator of manipulator cart 202 (e.g., by selecting a point on a map, by selecting one of a plurality of predetermined locations for manipulator cart 202 that are associated with different operations, etc.). In other examples, however, location 306-target may be automatically selected by system 100. For instance, location 306-target may be automatically selected in a manner that accounts for an operation type that is to be performed, photographic input representative of the room layout, a detected or expected location of cannulas on the body, gestures indicating the location by a person in a vicinity of the target area (e.g., gesturing by a bedside surgical team member), and/or any other criteria as may serve a particular implementation.

Other components of medical system 200 are also shown to be located in operating room 300 along with manipulator cart 202. For example, user control system 204 is shown to be statically located in another corner of operating room 300 in this example (although it will be understood that user control system 204 may, in certain examples, be mobile), and auxiliary system 206 is shown to similarly be moved from an initial storage or preparation location at the side of operating room 300 to a target location within sterile field 308 near operating table 302. It will be understood that other people and objects not explicitly shown may also be present within operating room 300, although, for purposes of this example, it is understood that there is not any significant obstacle on or near path 304 between locations 306-initial and 306-target.

In the scenario illustrated in FIG. 3, both locations 306-initial and 306-target are relatively proximate to one another within operating room 300. As such, path 304 has a clear beginning and a clear end and is fully contained within operating room 300. In other examples, however, it will be understood that one or both of the initial and target locations may not be located within the same room as one another, or the initial and/or target locations associated with a path may not yet be explicitly designated while manipulator cart 202 is navigating along the path. For instance, in one example, manipulator cart 202 may be located external to operating room 300 (e.g., in a different operating room, in a storage closet outside operating room 300, etc.) such that the initial location of manipulator cart 202 is external to room 300 and the target location (in this case, a location within room 300 where manipulator cart 202 will be draped and sterilized) is not designated until manipulator cart 202 enters operating room 300. Analogously, it will be understood that an initial location and a target location may be swapped so that manipulator cart 202 may be rolled back to a storage location or to another operating room, etc., after the operation at operating table 302 is complete.

Figure 4:
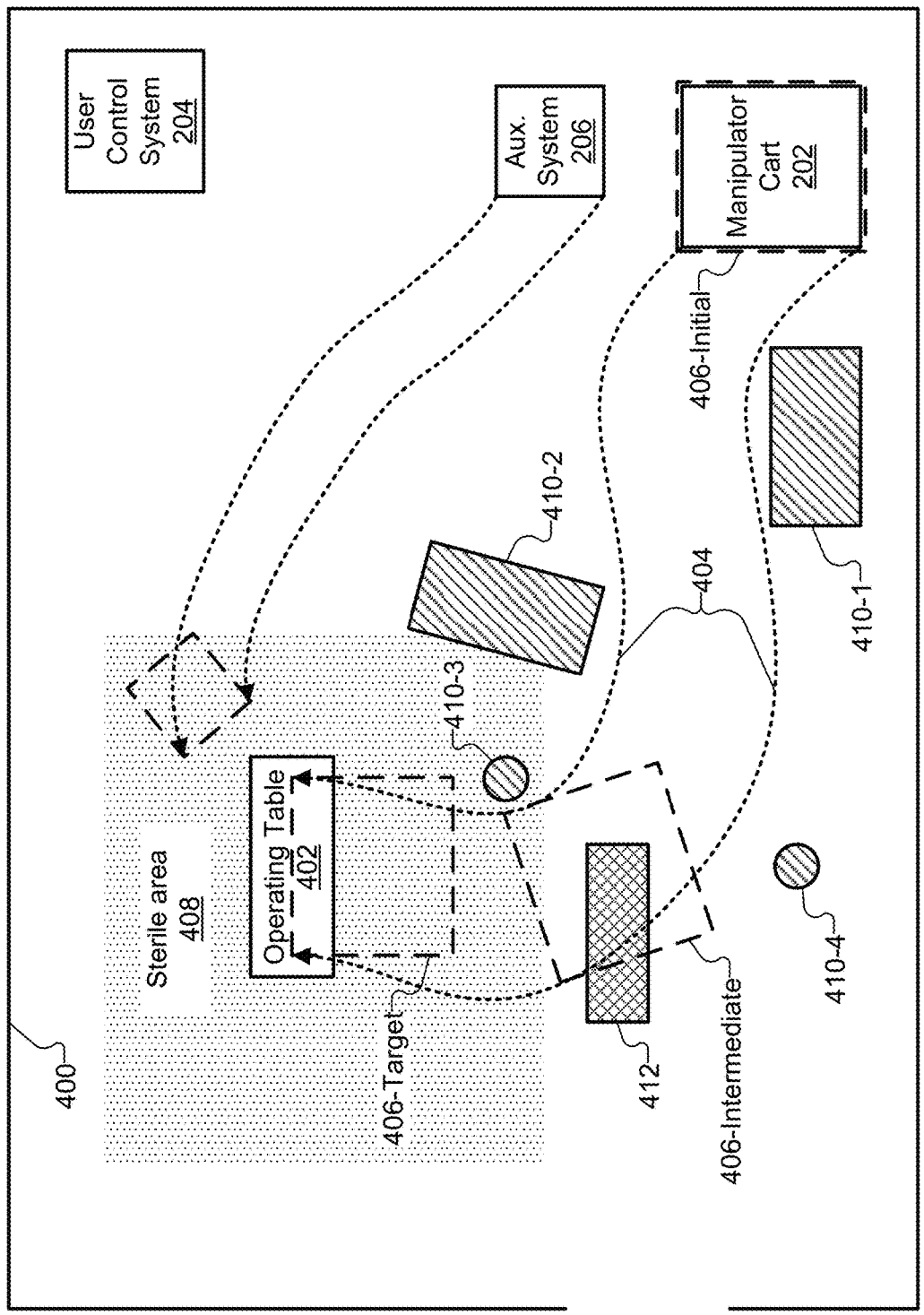

FIG. 4 shows another exemplary operating room 400 within which manipulator cart 202 is to be navigated toward an operating table 402 via an exemplary path 404 from an initial location 406-initial to a target location 406-target near operating table 402 within a sterile field 408. The scenario illustrated in FIG. 4 is similar to that shown in FIG. 3, and each the of the principles described in relation to FIG. 3 may similarly apply in the context of FIG. 4. However, operating room 400 of FIG. 4 is shown to be considerably more complex than operating room 300 of FIG. 3. For example, a plurality of obstacles 410 (e.g., obstacles 410-1 through 410-4) that must be avoided or otherwise accounted for in the planning of path 404 are located on the ground between locations 406-initial and 406-target. Moreover, an obstacle 412 that is shaded in with a different hatch-line pattern than obstacles 410 will be understood to represent an overhead obstacle that also must be accounted for in the defining of path 404.

As described above, system 100 may be configured to define path 404 from location 406-initial to location 406-target to thereby allow system 100 to autonomously control the steering of manipulator cart 202 as an operator controls the propulsion in a bifurcated navigation control mode. This path may be defined in any manner as may serve a particular implementation. For example, system 100 may further comprise (e.g. as part of or in addition to facilities 102 and 104) at least one sensor such as a visual light image sensor (e.g., a camera, a video capture device, etc.), an infrared image sensor, a depth sensor (e.g., a time-of-flight ("TOF") sensor, a Light Detection and Ranging ("LIDAR") sensor, an ultrasonic sensor, a radar sensor, a laser range finder, etc.), or any other sensor configured to detect characteristics of the natural world in a manner that facilitates the defining of a path for manipulator cart 202. Such sensors may be integrated with manipulator cart 202 itself (e.g., such as by being mounted on arms 212 or a base or other part of manipulator cart 202), or may be integrated with other components of medical system 200 or otherwise located in operating room 400 independently from manipulator cart 202 (e.g., mounted on the wall, attached to operating table 402, etc.).

In examples where system 100 includes or is in communication with one or more of these types of sensors, system 100 may perform the defining of path 404 by receiving sensor data from the at least one sensor and defining the path based on the received sensor data. For example, system 100 may receive image data and/or depth data from one or more vantage points and representative of real-time locations of obstacles 410 and/or 412. Consequently, system 100 may define path 404 in a manner that attempts to avoid or otherwise appropriately handle each of obstacles 410 and/or 412 that the sensors detect.

As system 100 plans and defines path 404 whereby manipulator cart 202 is to navigate from location 406-initial to location 406-target, system 100 may account for various factors. For example, system 100 may detect an obstacle between location 406-initial and location 406-target (e.g., one of obstacles 410 or 412), determine a movability status of the obstacle, and account for the movability status of the obstacle in the defining of path 404. As used herein, a "movability status" associated with an obstacle may refer to characteristics of the obstacle related to how easily the obstacle may be relocated, how much free space is around the obstacle, whether the obstacle is limited in movement by cables connected to the obstacle, how likely the obstacle is to relocate on its own (e.g., whether the obstacle is a person who appears to have awareness of manipulator cart 202 and is likely to move out of the way), and so forth.

Accordingly, accounting for a movability status of an easily movable obstacle (e.g., a stool, an observer, etc.) may be done differently than accounting for a movability status of a more permanent or non-movable obstacle (e.g., an anesthesiologist station that is set up near the operating table, etc.). For instance, an easily movable obstacle may be accounted for by routing the path to go through the obstacle and then indicating to the operator that the obstacle should be moved out of the way, while a more permanent or less conveniently-movable obstacle may be accounted for by routing the path around the obstacle to avoid the obstacle altogether. In other examples, certain obstacles may be determined to be likely to move on their own (e.g., a person who crosses over the path but has a clear movement vector indicating that they will not remain on the path for long, etc.) and, at least while the obstacles are not immediately proximate to the manipulator cart, may be treated as a lower priority to avoid or may be ignored by system 100 altogether in the defining of path 404. Additionally, certain overhead obstacles (e.g., obstacle 412) may be accounted for by lowering an operating platform of manipulator cart 202 to a boom and arms 212 are attached. By lowering the operating platform in this way, overhead obstacles may be passed under rather than needing to be routed around.

As another exemplary factor for which system 100 may account when defining path 404, system 100 may, after detecting an obstacle between location 406-initial and location 406-target, determine a risk factor, and account for the risk factor in the defining of path 404. As used herein, a "risk factor" may refer to anything related to an obstacle, a manipulator cart being navigated, the path being navigated, or any other aspect of the navigation that may be associated with adverse consequences. For example, one risk factor may be that if a speed of the propulsion is too high for a particular curve of the path, the manipulator cart could be at risk of tipping, causing damage to the manipulator cart. As another example, a risk factor associated with a particular obstacle may relate to consequences of the manipulator cart coming into contact with the particular obstacle as the manipulator cart traverses the path, thereby causing potential damage or a sterility breach to the manipulator cart and/or potential damage to the particular obstacle.

As such, accounting for a risk factor of an obstacle that is fragile or delicate, valuable or expensive to replace, or that is sterile and intended to remain so, may be done differently than accounting for a risk factor of an obstacle that is less consequential for manipulator cart 202 to come into contact with (e.g., a sterile object that a sterile manipulator arm may brush up against). For example, a delicate, expensive, or sterile obstacle may be accounted for by steering around the obstacle with a relatively wide margin to ensure that manipulator cart 202 does not contact the obstacle even if the obstacle moves or there is a miscalculation in navigating path 404. In contrast, an object that is not subject to any severe consequence if contacted by manipulator cart 202 (e.g., a stool that would just be bumped out of the way, etc.) may be accounted for by steering around the obstacle with a relatively narrow margin or no margin, thereby assuming the lower risk of negative consequence if minor contact is made.

In various examples, system 100 may account for obstacles by steering around the obstacles, requesting that the obstacles by manually moved (e.g., projecting a light of one color on an obstacle to be moved and a light of another color on obstacles that do not need to be moved), lowering the operating platform to pass under the obstacles, raising the operating platform so that arms attached to the boom pass over the obstacles, altering a pose of one or more arms (e.g., spreading or narrowing the spread of the arms, rotating the arms from one side of the cart to the other, lifting or lowering the arms, etc.), or in any other suitable way. Additionally, along with accounting for obstacles, system 100 may further account for other factors that affect the navigation of manipulator cart 202 along path 404. For example, system 100 may account for the width of manipulator cart 202 in determining a width of path 404 (e.g., including a margin), a turn radius of manipulator cart 202, which paths people moving about in operating room 400 tend to use to avoid obstacles, whether and how obstacles such as people are moving, how reconfigurable object surfaces are (e.g., distinguishing among solid, monolithic objects, objects with joints or flexible regions that allow bending and shape reconfiguration, objects covered by baggy drapes, etc.), and so forth.

In some implementations, system 100 may be configured to define and provide an operator with a plurality of path options, to thereby allow the operator to participate in the defining of path 404 by selecting one of the path options. Specifically, for example, the defining of path 404 by system 100 may include 1) defining a plurality of different paths whereby manipulator cart 202 could navigate from location 406-initial to location 406-target, and 2) selecting path 404 from the plurality of different paths and based on input from an operator. Additionally or alternatively, system 100 may request or accept additional operator input to define or revise path 404 in accordance with operator preferences.

In some scenarios (e.g., such as the relatively simple scenario illustrated in FIG. 3), it may be possible and desirable for system 100 to define an entire path (or a plurality of options for several entire paths) prior to manipulator cart 202 beginning to navigate along the path. In other examples, however, it may be difficult, impractical, impossible, or undesirable to define path 404 in its entirety at the outset in this way. This may be the case for a variety of reasons. For example, obstacles may be dynamically moving (e.g., some moving out of the way and others getting in the way after manipulator cart 202 has begun navigating). As another example, sensors may provide different characterizations (e.g., more comprehensive characterizations) from different locations along path 404 as different parts of the room become occluded or unoccluded from the vantage point of the sensors as the sensors move. Due to the dynamic and mobile nature of manipulator cart 202, as well as, in some examples, the dynamic and mobile nature of certain sensors and/or obstacles, system 100 may be configured to update path 404 while manipulator cart 202 is navigating along path 404, to dynamically provide different path options that may be identified or detected during navigation, or to otherwise dynamically alter path 404 as path 404 is being navigated.

System 100 may plan path 404 based on a predefined map of operating room 400 that system 100 accesses and that indicates the layout of operating room 400 (e.g., including wall placement, ceiling height and overhead obstacle height and layout, locations and configurations of permanent obstacles, the location and configuration of operating table 402, etc.). However, system 100 may also add to this predefined information a more dynamic analysis of temporary or new obstacles, dynamic docking considerations (e.g., detected locations of cannulas, etc.), and so forth. Sensors positioned in a manner that may be at least partially controlled by system 100 may be particularly useful for dynamic path definition. For example, sensors positioned on a boom or on individual arms 212 of manipulator cart 202 may be configured to continuously scan operating room 400 to capture new perspectives as manipulator cart 202 navigates along path 404. In some examples, system 100 may raise or lower an operating platform, rotate a boom to which arms 212 are attached, reposition a particular link or joint of an arm 212, or otherwise make adjustments to manipulator cart 202 in order to gather sensor data from different perspectives. In some examples, the predefined map of operating room 400 used by system 100 may have been generated (or may be generated in real time) by system 100 using simultaneous localization and mapping ("SLAM") techniques or other such techniques to build and update a three-dimensional model of operating room 400.

Even when system 100 has a degree of control over the sensors, it may not be possible in certain examples for system 100 to locate and positively identify location 406-target until manipulator cart 202 approaches the target location. As such, system 100 may direct, prior to the defining of path 404, manipulator cart 202 to be moved from a first location from which location 406-target is undetectable by a sensor of manipulator cart 202 to a second location from which location 406-target is detectable by the sensor. While manipulator cart 202 is at this second location, system 100 may determine that the sensor detects location 406-target and, in response to the determining that the sensor detects location 406-target, may designate the second location to be location 406-initial (i.e., the location at which path 404 begins).

FIG. 4 illustrates a path 404 that may be traversed by manipulator cart 202 by always using forward propulsion (i.e., moving in a forward direction). However, it will be understood that, in certain examples, an implementation of path 404 may be defined to include at least one portion in which manipulator cart 202 uses backward propulsion in order to progress along the path from the initial location to the target location. For example, the turning radius of the manipulator cart 202 may be larger than the radius of the turn needed by the path, and back-and-forth movement of the manipulator cart 202 while turning the manipulator cart 202 may allow the manipulator cart to achieve the sharper turn. As another example, an implementation of a path 404 may have a dead end from which manipulator cart 202 may need to be backed out (i.e., use backwards propulsion to move in a backwards direction) to traverse a new or revised path 404. In such examples, manipulator cart 202 may indicate to the operator that the operator should commanded propulsion in a reverse direction (e.g., begin pulling backwards rather than pushing forwards) in order to reach the target location. In further examples, a backwards portion of a path 404 may be planned into the path initially when the path is defined.

Medical system 200 is only shown to include a single manipulator cart 202 and, as shown by FIGS. 3 and 4, this manipulator cart 202 alone is presumed to perform manipulation tasks in connection with the operation being performed at operating tables 302 and 402. It will be understood, however, that in certain examples, more than one manipulator cart, or a manipulator cart and another equipment component of medical system 200, may both be navigated to the operating table for use in the operation. For example, medical system 200 may further include an additional equipment component besides manipulator cart 202 and the other equipment components illustrated in FIGS. 2-4, such as a second manipulator cart (e.g., a manipulator cart with more than, fewer than, or an equal number of, manipulator arms as manipulator cart 202), an equipment component that moves on a track or freely along a floor, an equipment component that moves through the air (e.g., a drone, etc.), or any other equipment component as may serve a particular implementation. In this example, the defining of the path may be performed to account for an additional path whereby the additional equipment component is to navigate from an additional initial location to an additional target location. For instance, path 404 may be defined so as to avoid not only obstacles 410 and 412, but also to not interfere with (or risk interference from) a path of one or more additional equipment components that may exist in a particular implementation of medical system 200 (not shown in FIG. 4). To this end, the defining of path 404 may account for the additional path based on locations of manipulator cart 202 and the additional equipment component, roles that manipulator cart 202 and the additional equipment component are to have in performing the operation at operating table 402, and so forth.

Along with locations 406-initial and 406-target, FIG. 4 also depicts an intermediate location labeled location 406-intermediate. As described above, system 100 may be configured to switch from a first bifurcated navigation control mode associated with a primary control interface to a second bifurcated navigation control mode associated with a secondary control interface upon reaching location 406-intermediate. Location 406-intermediate may be at any suitable location, including at an operator selected location (e.g., a preselected location, an arbitrary location at which an operator decides during the navigation to switch from the primary control interface to the secondary control interface, etc.) or a system-selected location (e.g., a location that is at a particular proximity from location 406-target, etc.).

In certain examples, location 406-intermediate may be associated with a boundary of sterile field 408, which, as shown, may include location 406-target while excluding location 406-initial. It will be understood that sterile field 408, as well as other sterile fields described herein, may be a relatively loosely defined area that is not so clear and specific as the area illustrated in FIG. 4 may suggest. For example, the back end of manipulator cart 202 may enter into the area drawn for sterile field 408 even if the back end of manipulator cart 202 may not be sterile. Accordingly, the "boundary" of sterile field 408 will be understood to not necessarily exist at a precise point or boundary in space, but, rather, may be associated with any location where a convenient handoff from a potentially non-sterile operator in a non-sterile part of the operating room to a sterile operator authorized to be in sterile field 408 may be made. Thus, as shown in the example of FIG. 4, location 406-intermediate may be depicted at a point where manipulator cart 202 begins entering sterile field 408 (i.e., at a location where a sterile operator who is standing by operating table 402 in preparation to assist in the operation may be close enough to provide an external stimulus to an arm 212 of manipulator cart 202 to thereby guide manipulator cart 202 the rest of the way to location 406-target using a secondary control interface, as will be described in more detail below). Location 406-intermediate may be associated with a boundary of sterile field 408 as a way of allowing non-sterile operators (i.e., operators who are not scrubbed in so as to be allowed within sterile field 408) to cooperate with sterile operators within sterile field 408 in navigating manipulator cart 202 all the way from location 406-initial to location 406-target. As such, any interactive physical components associated with the primary control interface may not be sterilized during the navigation of manipulator cart 202 along path 404 (i.e., such that a first operator performing the operator control using the primary control interface is not required to be sterilized), while any interactive physical components associated with the secondary control interface (e.g., an arm 212 used to guide manipulator cart 202 from location 406-intermediate to location 406-target) may be sterilized (i.e., such that the second operator performing the operator control using the secondary control interface is required to be sterilized).

Along with directing a base of manipulator cart 202 to be navigated along path 404 from location 406-initial to location 406-target, system 100 may similarly be configured, in addition or as an alternative to the navigation of the base, to navigate and move other components of manipulator cart 202 in accordance with a predefined or dynamically defined path (e.g., path 404). That is, during navigation of manipulator cart 202 toward location 406-target and/or once the base of manipulator cart 202 has arrived at location 406-target, system 100 may further direct manipulator cart 202 to be reoriented to a target orientation. Alternatively or in addition, during navigation of manipulator cart 202 toward location 406-target and/or once the base of manipulator cart 202 has arrived at location 406-target, system 100 may further direct other movable components of manipulator cart 202 (e.g., an operating platform, a boom, one or more manipulator arms 212, etc.) to become reoriented, posed, and otherwise reconfigured as part of, in addition to, or as an alternative to the navigation of path 404. For instance, in certain examples, initial location 406-initial may be associated with an initial configuration of a movable component of manipulator cart 202, target location 406-target may be associated with a target configuration of the movable component of manipulator cart 202, and the defining of path 404 may further include defining, with respect to path 404, a configuration plan whereby the movable component of manipulator cart 202 is to transform from the initial configuration to the target configuration.

Although FIGS. 3 and 4 have been described with initial and target locations for the manipulator cart 202, the technique described can also be applied to transition from an initial orientation to a target orientation of the manipulator cart 202, and from an initial configuration to a target configuration of the manipulator cart.

Figure 5:
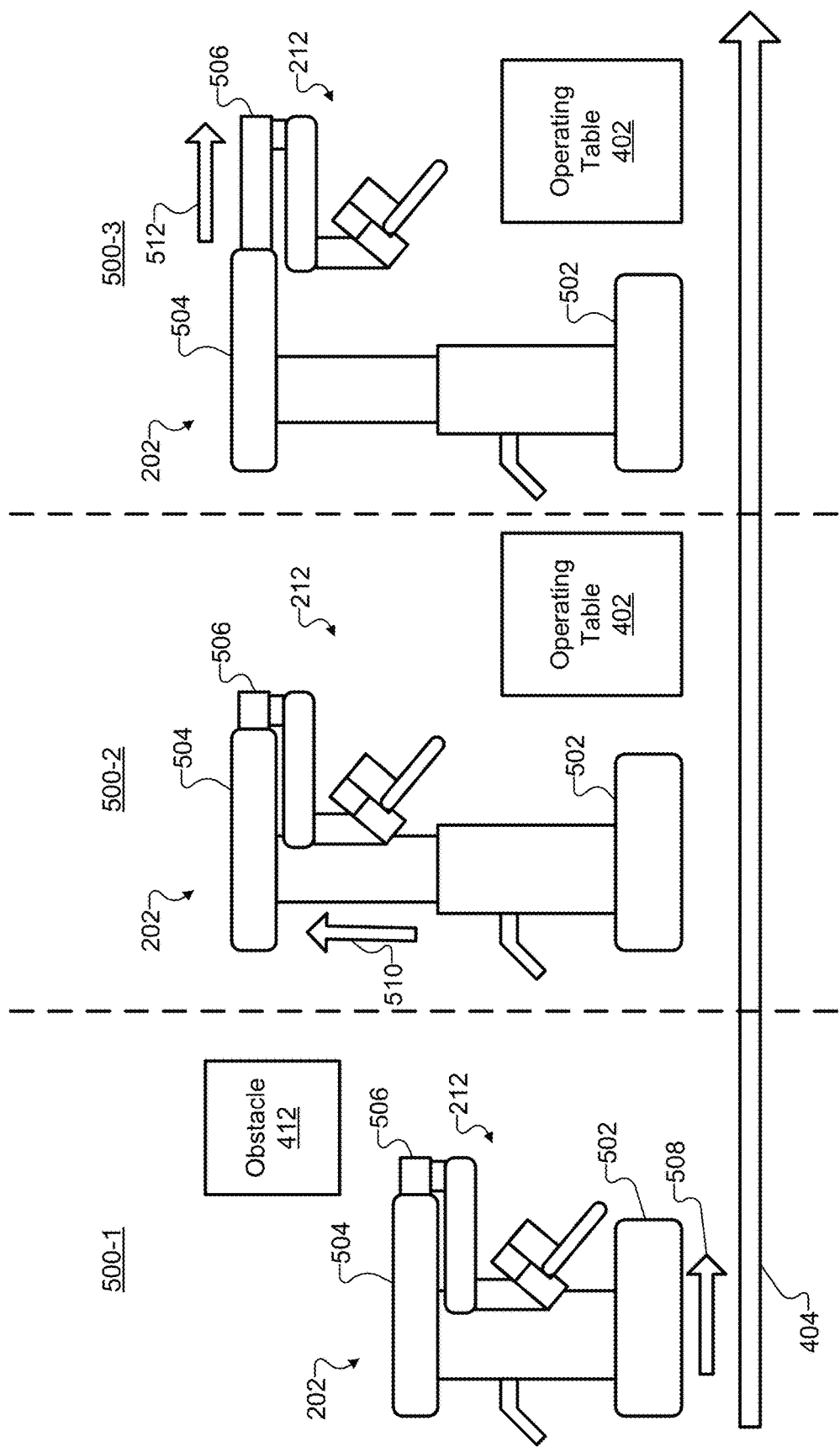
FIGS. 5 and 6 illustrate respective views of the exemplary manipulator cart as the manipulator cart navigates from the initial location and a corresponding initial configuration to the target location and a corresponding target configuration according to principles described herein.
Figure 6:
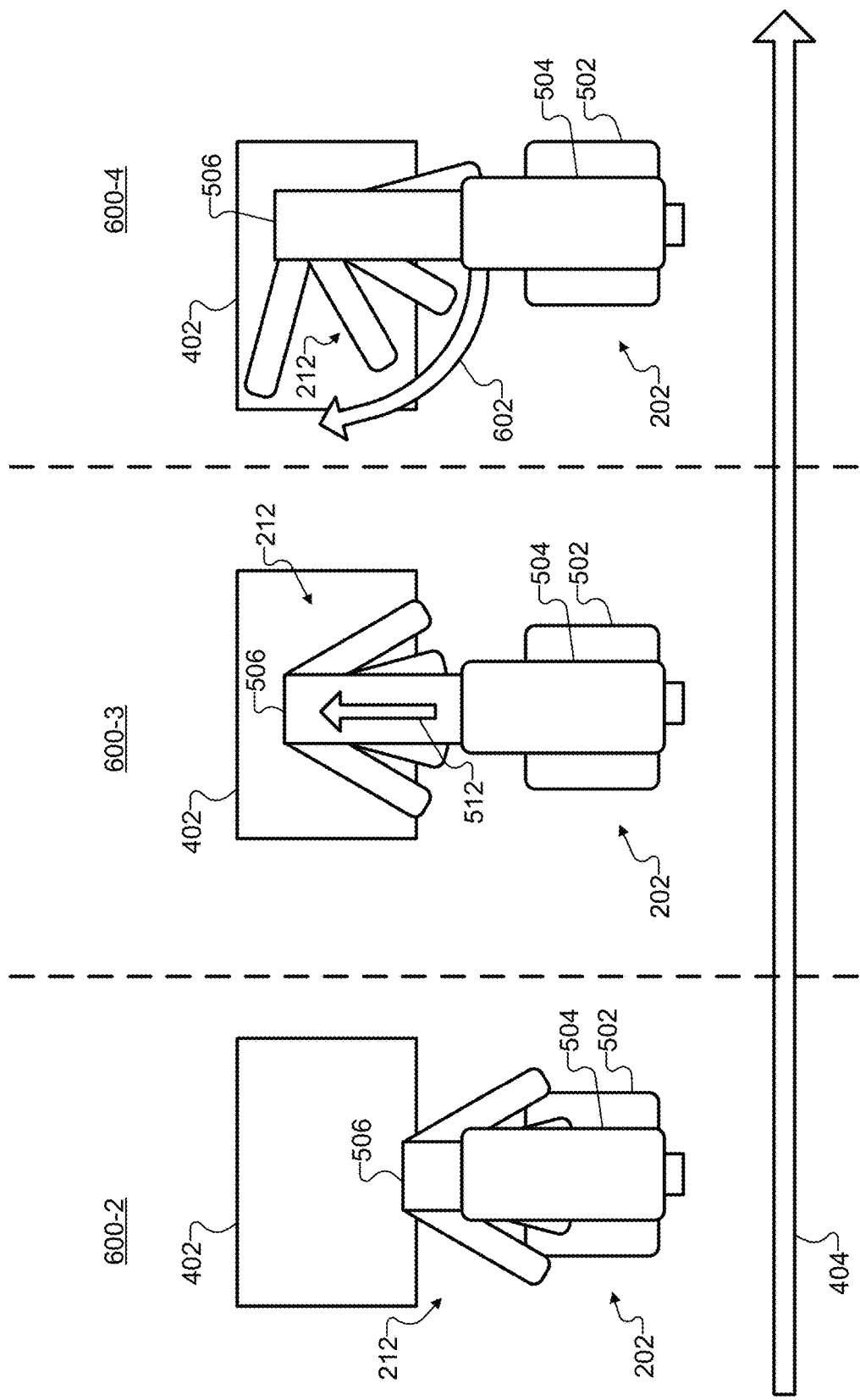

To illustrate, FIGS. 5 and 6 show, respectively, a series of side views and a series of top views of manipulator cart 202 as manipulator cart 202 navigates from location 406-initial and corresponding initial orientation and configuration to location 406-target and corresponding target orientation and configuration associated with path 404. Specifically, as shown in FIG. 5, a series of snapshots 500 (e.g., snapshots 500-1 through 500-3) depict manipulator cart 202 from a side view at three different points in time as manipulator cart 202 traverses path 404. Similarly, as shown in FIG. 6, a series of snapshots 600 (e.g., snapshots 600-2 through 600-4) depict manipulator cart 202 from a top view at three different points in time that will be understood to overlap with the points in time associated with snapshots 500. Specifically, snapshot 600-2 will be understood to depict a top view of manipulator cart 202 at the same point in time depicted by the side view of snapshot 500-2, and snapshot 600-3 will be understood to depict a top view of manipulator cart 202 at the same point in time depicted by the side view of snapshot 500-3.

Various movable components of manipulator cart 202 are labeled in each snapshot 500 and 600. Specifically, manipulator cart 202 is shown to have a base 502 that, when moved across the floor (e.g., driving on wheels or the like that are not explicitly shown), relocates the entire manipulator cart 202. Manipulator cart 202 is further shown to include an operating platform 504 that may be raised and lowered, and to which is attached a boom 506 that may be extended, retracted, pivoted, and so forth. One or more manipulator arms 212 are attached to boom 506 and may each be laterally translated, spread out, brought in, rotated, and/or manipulated in any other manner as may serve a particular implementation. It will be understood that other movable components not explicitly illustrated herein may also be present on manipulator cart 202 or on other manipulator cart implementations.

In some examples, the navigation of base 502 of manipulator cart 202 along path 404 may be planned and performed independently and separately in time from the reconfiguration of other movable components such as operating platform 504, boom 506, and/or arms 212. However, in other examples such as shown in FIGS. 5 and 6, a navigation plan and a configuration plan for manipulator cart 202 may be integrated together such that the navigation of base 502 along path 404 may be performed concurrently with the reconfiguration of the other movable components. In some examples, there may be a seamless and/or integrated transition between navigation control of base 502 and configuration control of other movable components. In certain implementations, these types of control may all be treated the same and may be considered to be part of the navigation along path 404. As such, manipulator cart 202 may not be considered to have completed navigation along path 404 until not only base 502 has arrived at location 406-target and orientated in a target orientation, but also operating platform 504, boom 506, arms 212, and other movable components of manipulator cart 202 have been properly positioned and configured to allow instruments to be connected to arms 212 and docked with cannulas associated with the body on operating table 402. In some instances, no further steps for configuring manipulator cart 202 may be necessary before manipulator cart 202 is ready to begin the medical operation. In other instances, further steps for configuring manipulator cart 202 (e.g., further adjustment of arms 212, adjustment of instruments connected to arms 212, etc.) may be appropriate before manipulator cart 202 is ready to begin the medical operation.

Snapshot 500-1 depicts a lateral movement 508 of base 502 along path 404. Movements such as movement 508 may ultimately result in manipulator cart 202 moving from location 406-initial to location 406-target, as described above. In snapshot 500-1, manipulator cart 202 is shown in an initial configuration that may be associated with a relatively small footprint of manipulator cart 202 (e.g. . . . , a minimized amount of space that manipulator cart 202 may take up) in which manipulator cart 202 may be configured when not in use (e.g., when being stored, etc.). As shown, in the initial configuration of snapshot 500-1, operating platform 504 may be completely lowered, boom 506 may be completely retracted, and arms 212 may be tucked away and brought in as much as possible. This initial configuration may be useful for navigating certain parts of path 404. For example, as shown, the initial configuration may allow manipulator cart 202 to pass under overhead obstacle 412 even though, if operating platform 504 were raised somewhat, manipulator cart 202 would not fit under overhead obstacle 412 and obstacle 412 would need to be steered around rather than passed under. Accordingly, path 404 may incorporate and be dependent upon the configuration plan of manipulator cart 202 in the sense that path 404 may be defined to have a requirement that manipulator cart 202 be in a particular configuration (e.g., the initial configuration) when manipulator cart 202 passes under obstacle 412. Analogously, path 404 may incorporate changes in the orientation of manipulator cart 202 to facilitate moving of the manipulator cart 202 to location 406-target.

In snapshots 500-2 (providing a side view) and 600-2 (providing a top view), manipulator cart 202 has arrived at operating table 402 and will be understood to be located at location 406-target such that base 502 has completed all the lateral movements (e.g., movement 508) defined for path 404. At this point in time, it may be desirable for arms 212 to be positioned over operating table 402, but, if manipulator cart 202 is still in the initial configuration of snapshot 500-1, arms 212 would be too low to the ground and would come into contact with operating table 402 if boom 506 were to be extended. Accordingly, as shown in snapshot 500-2, operating platform 504 may be raised by a movement 510 to lift arms 212 above operating table 402.

Thereafter, snapshots 500-3 (providing a side view) and 600-3 (providing a top view) illustrate that boom 506 may now be safely extended by a movement 512 until arms 212 are hovering over operating table 402. For example, boom 506 may be extended until laser crosshairs associated with an arm 212 associated with imaging equipment (e.g., an endoscope) becomes properly aligned with a target cannula that has been inserted into a body (not explicitly shown) on operating table 402. When this alignment is achieved, arms 212 may each be docked to a respective cannula and instruments may be attached to each arm 212 and inserted into the respective cannula. Once each arm 212 is docked with its respective cannula and any further steps to adjust components of manipulator cart 202 or to set up medical system 200 are complete, the medical operation to be performed by medical system 200 may begin.

In certain examples, arms 212 may need to be adjusted (e.g., spread, rotated, reconfigured, etc.) in order to become properly aligned with the cannulas in the manner described above. To illustrate, snapshot 600-4 shows how arms 212 may be spread out from one another and rotated in a movement 602 until each arm is properly aligned and ready for docking with a respective cannula so that the medical operation can begin. Once this final movement is complete, manipulator cart 202 may not only be located at location 406-target, but may also be in the target orientation and/or target configuration associated with the particular medical operation that is to be performed. As such, system 100 may determine and indicate to the operator (e.g., by way of visual, haptic, audible, or any other suitable type of feedback) that the navigation and configuration of manipulator cart 202 is complete.

As mentioned above, reconfiguration of one or more movable components of manipulator cart 202 may be performed separate in time from, or may be integrated with, the movement of base 502 along path 404. For example, in one implementation, the raising of operating platform 504 by movement 510 and the extending of boom 506 by movement 512 may be performed sequentially after movement 508 is complete and base 502 is parked at location 406-target. In other implementations, however, the raising of operating platform 504 by movement 510 and the extending of boom 506 by movement 512 may be performed concurrently with movement 508 and before base 502 has arrived at location 406-target. For example, movement 510 may be initiated as soon as obstacle 412 has been cleared (passed under) and movement 512 may be initiated as soon as operating platform 504 has been raised enough that arms 212 will not come into contact with operating table 402 or a body disposed thereon. In this way, additional valuable time in operating room 400 may be conserved as manipulator cart 202 may be in a location (and orientation and/or configuration as applicable) even sooner to begin the operation. Moreover, as an additional potential way of conserving time, respective instruments could be attached to arms 212 and docked with cannulas while movement 508 of base 502 is still ongoing in certain examples. The parallelizing of various movements associated with the navigation along path 404 in these ways will be described and illustrated in more detail below with respect to FIGS. 10 and 11.

While implementations have been described above that include both navigation and reconfiguration of movable components of manipulator cart 202, it will be understood that, in certain implementations, system 100 may only be tasked with navigation or reconfiguration of a manipulator cart, and not both. For instance, certain implementations of system 100 may only be configured to assist operators in steering a manipulator cart to a target location, or only configured to assist operators in steering the manipulator cart to a target location and orientation, and users may direct the configuration of other movable components of the manipulator cart without assistance from system 100 once the base of the manipulator cart is in position. As another example, an implementation of system 100 associated with a manipulator system that is, for example, attached bedside to an operating table or that is configured to be moved along a physical track or the like, may not benefit from navigation assistance of system 100. Rather, such a manipulator system may benefit only from assistance of system 100 in configuring movable components such as an operating platform, a boom, and/or manipulating arms.

As described above, system 100 may direct manipulator cart 202 to navigate along different portions of path 404 in different bifurcated navigation control modes. For example, as described above, system 100 may direct manipulator cart 202 to navigate from location 406-initial to location 406-intermediate in a first bifurcated navigation control mode associated with a primary control interface, and may direct manipulator cart 202 to navigate from location 406-intermediate to location 406-target in a second bifurcated navigation control mode associated with a secondary control interface.

Figure 7:
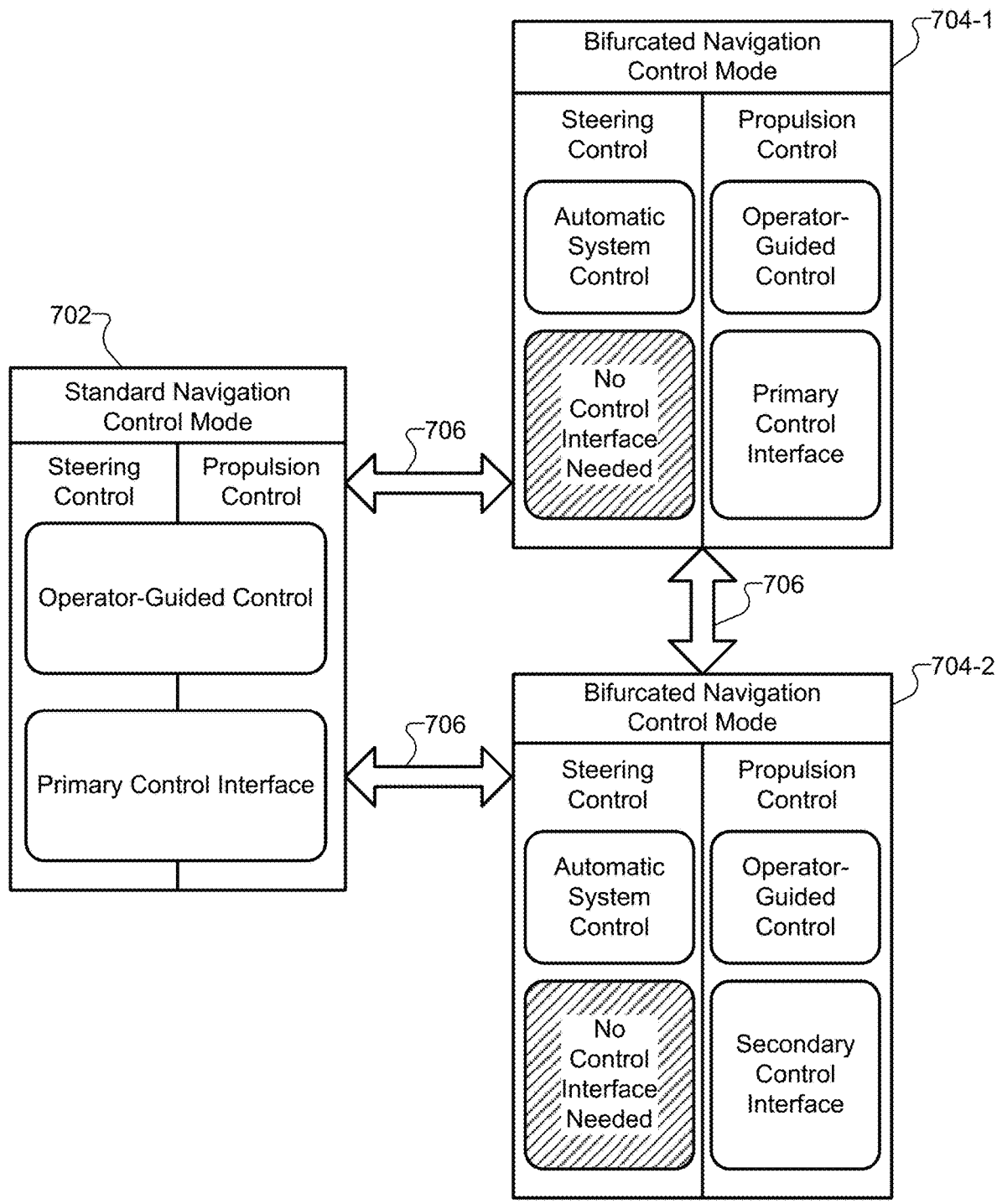
FIG. 7 illustrates various exemplary navigation control modes that may be employed as the manipulator cart navigates from the initial location to the target location according to principles described herein.

To illustrate, FIG. 7 shows various exemplary navigation control modes that may be employed as manipulator cart 202 navigates from location 406-initial to location 406-target. Specifically, FIG. 7 shows representations of a standard navigation control mode 702 and two different bifurcated navigation control modes 704 (bifurcated navigation control modes 704-1 and 704-2). In each navigation control mode representation depicted in FIG. 7, an indication is given of who or what controls the steering and the propulsion of manipulator cart 202 by labels indicating "Automatic System Control" (i.e., control by system 100) or "Operator-Guided Control" (i.e., control by a human operator) being placed, as appropriate, in columns for steering ("Steering Control") and propulsion ("Propulsion Control"). Additionally, for each instance of operator-guided control in the representations of FIG. 7, an indication is given of which control interface is to be used by the operator to exert the control (e.g., the "Primary Control Interface" or the "Secondary Control Interface").

It will be understood, as will be described in more detail below, that at certain times, both a primary and a secondary control interface may be used by two different operators at once, and commands from one control interface may be prioritized over commands from the other. In certain implementations, this situation could occur within yet another bifurcated navigation control mode 704, while, in other implementations, such concurrent use of the primary and secondary control interfaces may be handled in one of bifurcated navigation control modes 704-1 or 704-2, or a modified version thereof. Additionally, as shown by labels indicating "No Control Interface Needed," any commands received from an operator by way of either the primary or the secondary control interface may be effectively ignored and not used for control because control is being handled by system 100.

As shown, standard navigation control mode 702 is characterized by allowing operator control of both the steering and the propulsion of manipulator cart 202 using the primary control interface. Standard navigation control mode 702 is the control mode conventionally employed for navigating manipulator carts from initial to target locations and/or orientations. In contrast, bifurcated navigation control modes 704 are each characterized by bifurcating the steering and propulsion control, allowing operator control of only the propulsion while the steering is controlled by system 100 automatically. The difference between bifurcated navigation control modes 704-1 and 704-2 relates to which control interface is used for the operator control. Specifically, a primary control interface may be employed in bifurcated navigation control mode 704-1, and a secondary control interface may be employed in bifurcated navigation control mode 704-2.

The primary control interface may be any suitable control interface configured to facilitate operator control of both steering and propulsion of manipulator cart 202. As such, and as shown in FIG. 7, the primary control interface used to provide proportion control in bifurcated navigation control mode 704-1 may be the same control interface used conventionally to provide both steering and propulsion control in standard navigation control mode 702. For instance, in certain examples, the primary control interface may include a handlebar-based control interface integrated into manipulator cart 202, or one or more other suitable control mechanisms (e.g., a steering wheel, a joystick, a touch screen control panel, a remote control, a throttle, etc.).

Figure 8:
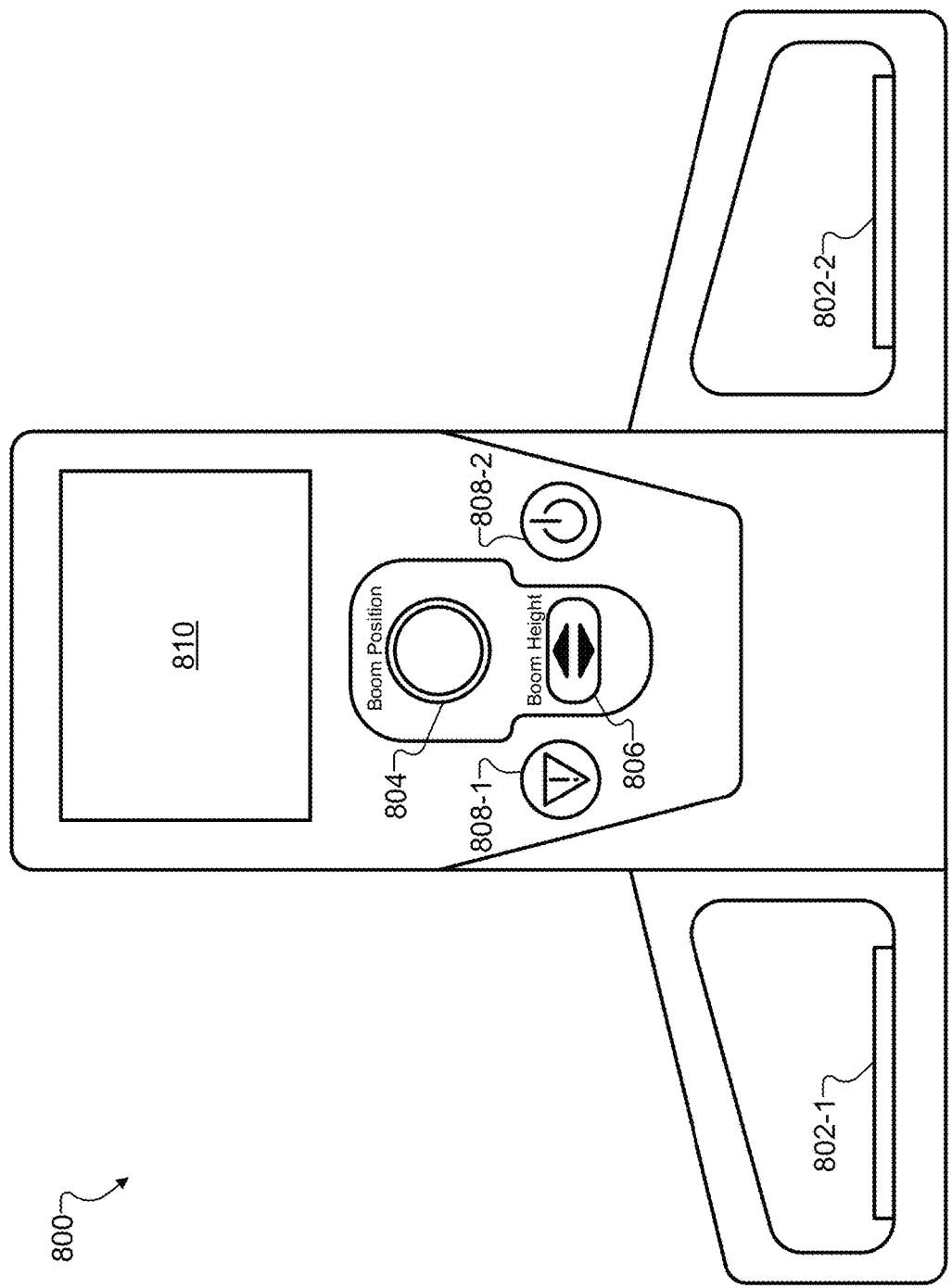
FIG. 8 illustrates exemplary components of a primary control interface that may be employed during navigation of the manipulator cart from the initial location to the target location according to principles described herein.

To illustrate, FIG. 8 shows exemplary components of a primary control interface 800 that may be employed during navigation of manipulator cart 202 from at least location 406-initial to location 406-intermediate. As shown, primary control interface 800 is implemented as a handlebar-based control interface integrated into manipulator cart 202 (i.e., built into manipulator cart 202 such as on the opposite side of manipulator cart 202 from arms 212). FIG. 8 shows various controls that may be included in primary control interface 800 in a particular implementation. Specifically, primary control interface 800 is shown to include drive switches 802 (i.e., drive switches 802-1 and 802-2) built into handlebars that allow an operator to conveniently steer and/or direct propulsion of manipulator cart 202. For example, in standard navigation control mode 702, one or both of drive switches 802 may be pressed to cause manipulator cart 202 to drive forward, and turns may be directed by the user pulling or pushing the handlebars to one side or the other. The handlebars and drive switches 802 may thus be used to steer and direct propulsion of manipulator cart 202 along a path such as path 404.

Other controls included within primary control interface 800 may facilitate operator-guided movement of other movable components of manipulator cart 202. For example, primary control interface 800 includes a boom position knob 804 that may be pushed forward to extend boom 506 (e.g., such as illustrated by movement 512), pulled backwards to retract boom 506, pushed left or right to pivot boom 506, or turned clockwise or counterclockwise to rotate arms 212 on boom 506 (e.g., such as illustrated by movement 602). As another example, primary control interface 800 is shown to include a boom height rocker switch 806 that, when pushed forward may raise operating platform 504 (e.g., such as illustrated by movement 510), and when pulled backward may lower operating platform 504. Additionally, as further shown, primary control interface 800 may include various buttons 808 (e.g., buttons 808-1 and 808-2) used to input an emergency stop command (button 808-1), power on and off manipulator cart 202 (button 808-2), or perform other operations as may serve a particular implementation. While a few specific input controls are explicitly shown in FIG. 8 for illustration, it will be understood that more or fewer controls that perform similar or different functionality as described above may be included on other implementations of primary control interface 800.

Along with the controls described above, primary control interface 800 is shown to further include a touchscreen 810 used to accept other types of input commands (e.g., based on user selection of touchscreen panels) and to provide output information to the operator. Specifically, touchscreen 810 may provide visual feedback to the operator, while other suitable output mechanisms such as loudspeakers, actuators, LEDs, buzzers, etc., may be used to provide visual and/or other types of feedback (e.g., audible feedback, haptic feedback, etc.). It will be understood that, in certain examples, touchscreen 810 may not include a touch panel, but, rather, may be implemented only as a display monitor capable of outputting information and not accepting operator input. In still other examples, a primary control interface may be implemented exclusively by buttons, knobs, and/or other controls, and may not include any display monitor or touch screen.

Various types of feedback may be provided to an operator by way of touchscreen 810 and/or other output mechanisms of primary control interface 800. For example, system 100 may provide, to an operator performing operator control of manipulator cart 202 by way of primary control interface 800, one or more status indicators. For example, the status indicators may indicate a progression of manipulator cart 202 along path 404, whether manipulator cart 202 has completed navigating the path, and so forth. The status indicators may take any form as may serve a particular implementation. For example, one status indicator may indicate what percentage of path 404 has been traversed and indicate when manipulator cart 202 arrives at location 406-target and/or completes path 404. As another example, another status indicator may show (e.g., from a top view) a depiction of path 404 (e.g., including locations 406-initial and 406-target, obstacles 410 and/or 412, etc.) so as to indicate a current location of manipulator cart 202 on path 404. In some examples, after manipulator cart 202 has arrived at location 406-target and has stopped, the status indicator may continue to indicate that manipulator cart 202 has not completed navigating path 404 until a target orientation has been achieved, and/or until each movable component has been properly configured according to the configuration plan.

Other types of feedback provided by way of primary control interface 800 may include a current position of manipulator cart 202 shown on a map of path 404 (e.g., a map indicating turns, obstacles shown in different colors, etc.), an indication that navigation has stopped short, an indication that navigation has been attempted to continue forward after navigation was complete, and/or 2D photographic imagery or 3D model imagery captured by or derived from sensors on manipulator cart 202 (e.g., imagery depicting ports and/or cannulas being approached). Moreover, primary control interface 800 may provide feedback when system 100 switches from a dynamically-generated path to a full pre-defined path (e.g., when location 406-target is identified and a path all the way to location 406-target and/or to a final target configuration is defined), when control switches from one control interface to another, or when the navigation control mode switches (e.g., from the standard navigation control mode to a bifurcated navigation control mode, from one bifurcated navigation control mode to another, etc.). As another example, primary control interface 800 may provide feedback showing regions where manipulator cart 202 may park (e.g., a target location or a range of potential target locations), feedback indicating a range of motion of various movable components of manipulator cart 202, an indication of when sterile field 408 has been entered by manipulator cart 202, an indication of which navigation control mode is currently in use, and/or an indication of which direction manipulator cart 202 is moving or is supposed to be moving according to path 404.

Haptic or other feedback may also be provided to signal to an operator to give up or take control. For instance, primary control interface 800 may provide an indication to a non-sterile operator that a sterile operator is to take control (e.g., using the primary or secondary control interface) when manipulator cart 202 comes within a certain proximity of operating table 402, when manipulator cart 202 enters sterile field 408, or when some other threshold or criteria is detected to have been satisfied. In some examples, an intermediate location may be indicated where a handoff from one operator to another is suggested or required. For example, in a particular location or along a particular length of path 404, control may be performed by either the primary or the secondary control interface, or a particular control interface may be required to progress beyond a particular location.

Haptic or other feedback may also be provided to operators of manipulator cart 202. For instance, rather that providing visual feedback by way of touchscreen 810, system 100 may use boom 506, arms 212, or another such component of manipulator cart 202 to, for example, point in the direction that manipulator cart 202 is currently steering. It will be understood that certain of the types of feedback described above may be provided in one or more ways other than the ways explicitly described herein (e.g., visually, audibly, haptically, etc.). Additionally, it will be understood that certain types of feedback described above may be provided not only by primary control interface 800, but also by a secondary control interface, such as will now be described in more detail.

Returning to FIG. 7, the representation of bifurcated navigation control mode 704-2 shows that a secondary control interface may be used for operator guided control of the propulsion of manipulator cart 202 (instead of primary control interface 800) when system 100 operates in bifurcated navigation control mode 704-2. The secondary control interface may be any suitable control interface configured to facilitate operator control of the propulsion but not the steering of manipulator cart 202. In other words, the secondary control interface may be an auxiliary control interface that is suitable and convenient for use in a bifurcated navigation control mode such as bifurcated navigation control mode 704-2, but that might not be suitable for use in standard navigation control mode 702. For instance, in certain examples, the secondary control interface may not be configured to facilitate operator control of steering of manipulator cart 202, but, rather, may only accept forward propulsion commands (possibly with a desired speed and possibly providing feedback to the operator that forward propulsion is about to begin or is ongoing), backward propulsion commands (possibly with a desired speed and possibly providing feedback to the operator that backward propulsion is about to begin or is ongoing), and stop commands (possibly providing feedback to the operator that propulsion is about to stop or is already stopped).

For instance, one exemplary secondary control interface may be a gesture-based control interface. Such a control interface may be associated with an image sensor, for example, and may be configured to facilitate the control of the propulsion of manipulator cart 202 by: 1) accessing (e.g., by way of the image sensor) an image of an operator (e.g., a sterile operator standing in front of manipulator cart 202 near operating table 402) performing a control gesture, 2) determining whether the control gesture performed by the operator is a forward propulsion gesture, and 3) determining whether the control gesture performed by the operator is a backward propulsion command. Because steering is controlled by system 100 in bifurcated navigation control mode 704-2, determining whether a forward or backward propulsion command is being provided by the operator may be sufficient to allow system 100 to direct navigation of manipulator cart 202 from location 406-intermediate to location 404-target.

Gestures used in a gesture-based control interface may be detected by way of one or more image capture devices mounted on manipulator cart 202 or in other suitable places within operating room 400. Gestures may be predefined to be any suitable gesture such as a continuous beckoning with a hand or finger, a continuous wave, or the like. In some examples, an explicit stop gesture (e.g., a flat palm or the like) may be defined. Additionally or alternatively, system 100 may interpret an absence of either a continuous forward or backward gesture as a stop command (i.e., an indication that manipulator cart 202 should not continue forward on path 404 for the time being). Along with indicating a basic forward or backward propulsion command, gestures may further be used to indicate a basic propulsion speed. For example, a relatively fast continuous wave of the hand may be interpreted as a forward propulsion command associated with a relatively fast speed, while a relatively slow continuous wave may be interpreted as a forward propulsion command associated with a relatively slow speed.

Another exemplary secondary control interface may be a voice-controlled interface. Such a control interface may include a microphone, for example, and may be configured to facilitate the control of the propulsion of manipulator cart 202 by: 1) capturing (e.g., by way of the microphone) a voice command provided by an operator (e.g., a sterile operator), 2) determining whether the voice command is a forward propulsion command, and 3) determining whether the voice command is a backward propulsion command. Again, because steering is controlled by system 100 in bifurcated navigation control mode 704-2, determining whether a forward or backward propulsion command is being provided by the operator may be sufficient to allow system 100 to direct navigation of manipulator cart 202 from location 406-intermediate to location 404-target.

Voice commands provided by way of a voice-controlled interface may be predefined to be any suitable voice commands such as a continuous repetition of a word or phrase, or the like. In some examples, an explicit stop voice command may be defined. Additionally or alternatively, system 100 may interpret an absence of any words or of any particular voice command as a stop command. Along with indicating a basic forward or backward propulsion command, voice commands may further be used to indicate a basic propulsion speed.

Yet another exemplary secondary control interface that may be employed in bifurcated navigation control mode 704-2 may be an arm-guided interface in which an operator guides manipulator cart 202 by pulling or pushing on a particular manipulator arm 212. To implement an arm-guided interface, manipulator cart 202 may include a set of one or more arms (e.g., manipulator arms 212 described above), and the secondary control interface may be implemented using a portion of a designated arm of the set of one or more arms 212. For example, the secondary control interface may be configured to facilitate the control of the propulsion by: 1) sensing an external stimulus applied to the portion of the designated arm, and 2) in response to the sensed external stimulus meeting a set of criteria, interpreting the sensed external stimulus as a propulsion command (e.g., either a forward or a backward propulsion command).

The portion of the designated arm used to provide guidance to control the propulsion of manipulator cart 202 along path 404 may be any suitable portion of any suitable arm. For example, the portion may include a link and/or a joint, or may include a plurality of links and/or joints of a particular manipulator arm 212 of manipulator cart 202. In some examples, an implementation of manipulator cart 202 may include a single manipulator arm, such that the set of one or more arms includes only one manipulator arm 212. In such cases, it may be clear which arm is to be used to direct the propulsion control since there is only one choice. In other examples such as illustrated above, however, the set of one or more arms of manipulator cart 202 may include a plurality of arms (e.g., four arms in the examples shown above). In these cases, the designated arm may be the only arm of the plurality of arms that is designated for implementing the secondary control interface. As such, system 100 may be configured to indicate to an operator which arm of the plurality of arms is the designated arm. For example, system 100 may cause the designated arm to be visually differentiated from another arm (or from other arms) in the plurality of arms so as to make the designated arm identifiable by the operator as the designated arm included in the secondary control interface.

Figure 9:
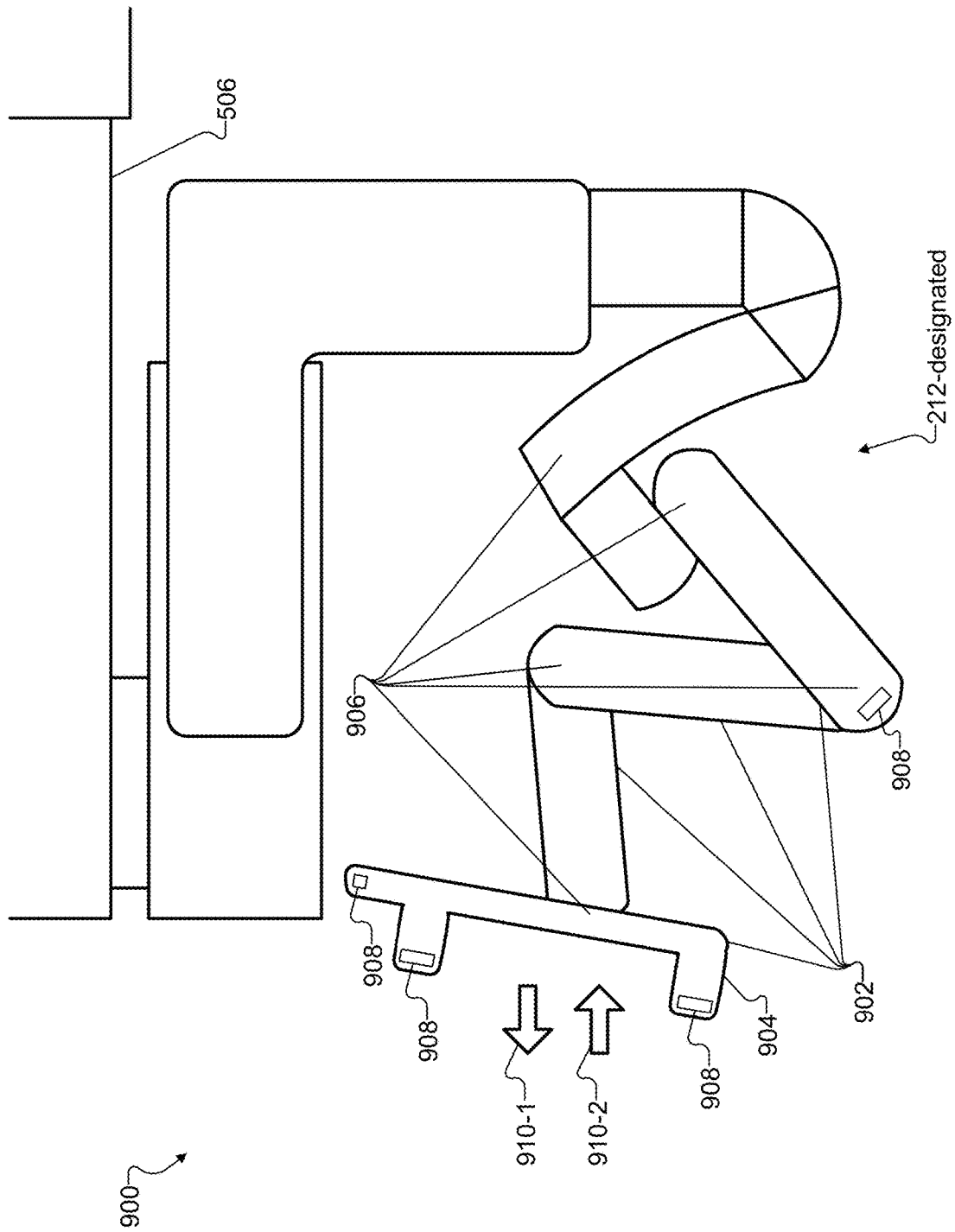
FIG. 9 illustrates exemplary components of a secondary control interface that may be employed during the navigation of the manipulator cart from the initial location to the target location according to principles described herein.

To illustrate, FIG. 9 shows exemplary components of a secondary control interface 900 that may be employed during the navigation of manipulator cart 202 from at least location 406-intermediate to location 406-target. In some embodiments, the secondary control interface 900 may also be employed during the orientation and/or configuration of manipulator cart 202 to target orientations and/or configurations. More specifically, FIG. 9 depicts a particular designated arm 212-designated that is attached to boom 506 of manipulator cart 202. Arm 212-designated is shown to comprise a plurality of links 902 including a manipulator link 904 (i.e., a distal link configured to hold a manipulator tool), and a plurality of joints 906. As mentioned above, any combination of links 902 and/or joints 906 (including links 902 and/or joints 906 that are not explicitly shown or labeled in FIG. 9) may form the portion of arm 212-designated used by the operator to provide guidance to control the propulsion of manipulator cart 202. For instance, in certain implementations, the operator may pull or push on manipulator link 904 to thereby apply an external stimulus (e.g., a force, a torque, a joint deflection, etc.) to one or more joints 906 that may be sensed by system 100 and interpreted as a forward propulsion command, a backward propulsion command, or the like.

System 100 may designate arm 212-designated based on which arm 212 an operator is detected to exert a force on (thereby essentially allowing the operator to designate which arm 212 to use), or may automatically determine which arm 212 is to be used and cause that arm 212 to be visually differentiated from one or more other arms 212 to indicate to the operator that it is the arm to be used to provide the propulsion control. Arm 212-designated may be visually differentiated using any aspect of the color, shape, size, pose, position, motion, or other suitable characteristic of arm 212-designated. As one example, system 100 may cause arm 212-designated to be visually differentiated from one or more other arms that may be present by use of one or more visual indicators 908, which may be implemented as colored light-emitting diodes ("LEDs") or the like. For example, system 100 may cause indicators 908 to be one color (e.g., red, orange, etc.) when secondary control interface 900 is unavailable (e.g., when primary control interface 800 is still being used) and/or if this particular arm is not designated as the arm to be used in the secondary control interface in a particular situation. Conversely, system 100 may cause indicators 908 to be a different color (e.g., green, blue, etc.) under different circumstances such as when secondary control interface 900 is available and arm 212-designated is designated as the arm to be used for secondary control interface 900. In other examples, other indicator features (e.g., LED pulse rate, etc.) may be used instead of or in addition to color to provide similar status indications.

Employing visual indicators such as indicators 908 may be an advantageous way for system 100 to visually differentiate arm 212-designated because indicators 908 may be illuminated independently of the pose of arm 212-designated. This independence is advantageous because, in some examples, arm 212-designated may be associated (as with other manipulator arms 212 included on manipulator cart 202) with a target configuration that must be achieved before the navigation of manipulator cart 202 will be complete (i.e., a final pose in which the arm is configured for docking with a cannula). As such, it may be desirable for arm 212-designated to remain unclutched (e.g., stiffly engaged in place in a desired pose using brakes or active servo control of various joints 906) as external stimulus is applied to arm 212-designated. Additionally or alternatively, arm 212-designated may be configured to compromise its pose to some degree (e.g., allowing manipulator link 904 to be pulled up to a threshold amount forward with respect to base 502 of manipulator cart 202), but to thereafter restore the same pose by navigating and/or reconfiguring manipulator cart 202 (e.g., by driving manipulator cart 202 up to the same threshold amount to restore the spatial relationship of base 502 with manipulator link 904). A method of visual differentiation that does not require a configuration change of arm 212-designated may advantageously allow arm 212-designated to remain stiff, to absorb deflections, and/or to otherwise maintain or restore its pose in any of these ways.

In spite of these potential advantages in certain implementations, however, it will be understood that, in other implementations, system 100 may visually differentiate arm 212-designated in other suitable ways (e.g., ways that may or may not involve indicators 908) that may be appropriate and desirable for those implementations. For example, arm 212-designated may be floated (i.e., clutched so as to be easily reconfigurable rather than stiffly kept in place) in a way that other arms 212 are not, may be presented to the operator in a different manner than other arms are presented (e.g., by being held out in front of the other arms), or in any other manner as may serve a particular implementation.

If arm 212-designated is to remain substantially stiff and unclutched as an operator imposes an external stimulus on arm 212-designated (e.g., by pushing or pulling on manipulator link 904 or the like), system 100 may be configured to temporarily disable (e.g., while arm 212-designated is in use for secondary control interface 900) a breakaway clutch feature that would normally allow arm 212-designated to be manually reconfigured in a manner similar to if the operator intentionally engaged a dedicated clutching button. Alternatively, system 100 may be configured without such a breakaway clutch feature.

In other examples, rather than disabling the breakaway clutch feature, system 100 may be configured to differentiate between external stimulus intended to perform propulsion control of manipulator cart 202 and external stimulus intended to engage the breakaway clutch feature. This differentiation may be implemented in any suitable way, including by limiting the clutching features for arm 212-designated in comparison to clutching features provided for other arms of manipulator cart 202. For example, breakaway clutching may be more compact, or arm 212-designated may need to be forced further outside of a normal range to engage the breakaway clutch (rather than to provide propulsion commands). In still other examples, indicators 908 may flash in a certain color or pattern to help the operator know which functionality is active, or the like.

Regardless of whether the breakaway clutch is temporarily disabled while arm 212-designated is used for secondary control interface 900, left enabled but modified in function while arm 212-designated is used for secondary control interface 900, or handled in another way, various safety features normally implemented in conjunction with clutch mode (e.g., including for the breakaway clutch) may continue to be leveraged for arm 212-designated. For example, as arm 212-designated is either clutched or used to provide propulsion control, velocity limits, high-frequency disturbance rejection, calibrated gravity compensation, friction compensation, and so forth, may be implemented for arm 212-designated.

System 100 may interpret any suitable external stimulus provided by an operator as any suitable propulsion command. For example, the external stimulus may be a deflection of the portion of arm 212-designated, a force or torque applied to a link 902 or joint 906 of arm 212-designated, or another external stimulus as may serve a particular implementation.

If system 100 detects that any of these types of external stimulus meets a set of criteria, system 100 may interpret the sensed external stimulus as a propulsion command 910 (e.g., a forward propulsion command 910-1, a backward propulsion command 910-2, or another suitable propulsion command not explicitly shown). For example, the set of criteria may include a criterion based on a direction of the external stimulus (e.g., whether the operator is pushing or pulling on the portion of arm 212-designated, whether the stimulus is substantially parallel or anti-parallel to the direction of path 404 or is substantially orthogonal to the direction of path 404, etc.). If the direction of the external stimulus is a substantially forward direction (e.g., if the operator is pulling on arm 212-designated in a direction substantially parallel to the direction of path 404), system 100 may interpret the external stimulus as forward propulsion command 910-1. Conversely, system 100 may interpret the external stimulus as backward propulsion command 910-2 in response to the direction of the external stimulus being in a substantially backward direction (e.g., if the operator is pushing back on arm 212-designated in a direction substantially anti-parallel to the direction of path 404). If the external stimulus is not substantially parallel or anti-parallel to the direction of path 404, system 100 may interpret the external stimulus as an attempt by the operator to clutch arm 212-designated or to steer manipulator cart 202 in a direction other than path 404, which may trigger a switch to the standard navigation control mode or may be ignored (e.g., if the secondary control interface is not configured to facilitate steering).

In some implementations, the external stimulus is interpreted to be a forward propulsion command 910-1 in response to the direction of the external stimulus being directed substantially forward along path 404 toward location 406-target, rather than, for example, having a significant component of force applied in a direction substantially orthogonal to path 404. For instance, system 100 may determine that the direction of the external stimulus is directed "substantially forward" along path 404 toward location 406-target when a parallel component of the external stimulus (i.e., a component pointing toward following a remainder of path 404 for manipulator cart 202 to move to location 406-target) is greater than an anti-parallel component (i.e., a component pointing oppositely from the parallel component along the portion of path 404 that manipulator cart 202 has already navigated from location 406-initial). In other examples, system 100 may determine that the direction of the external stimulus is directed "substantially forward" along path 404 toward location 406-target when the parallel component of the external stimulus is greater than a predetermined threshold. Because arm 212-designated is not a monolithic entity, but, rather, is constructed of multiple links 902 and joints 906, there may be situations when external stimulus applied to one link or joint is opposite in direction or otherwise inconsistent with external stimulus applied to another link or joint. Accordingly, other rules may be set forth to further define what is to be interpreted as a "substantially forward" external stimulus in relation to specific thresholds for particular links 902 and joints 906. In other examples, this potential ambiguity may be addressed by requiring users to apply force to arm 212-designated at a clutch button.

In like manner as described above in relation to interpreting a propulsion command 910 in response to the direction of the external stimulus being substantially forward along path 404, system 100 may also be configured to not interpret an external stimulus as a propulsion command 910 in response to the direction of the of the external stimulus being substantially orthogonal to path 404 toward location 406-target. For example, if an orthogonal component of the external stimulus is greater than a forward or backward component of the external stimulus, or greater than a predefined threshold, system 100 may ignore the external stimulus and not interpret the external stimulus as a propulsion command 910.

Along with these direction-based criteria, system 100 may also consider other exemplary criteria in the set of criteria when determining whether sensed external stimulus is to be interpreted as a propulsion command 910. For example, the set of criteria may include a magnitude of the external stimulus being greater than a threshold magnitude, a frequency of the external stimulus being lower than a threshold frequency (or being within a predetermined threshold frequency range), or the like. In this way, very low magnitude or low frequency external stimulus (e.g., such as may be detected based on gravity or another source other than an intentional external stimulus applied by an operator) may not be interpreted as a propulsion command 910. Additionally, such criteria may ensure that high frequency external stimulus (e.g., such as may be detected if arm 212-designated unintentionally collides with an obstacle) may similarly not be misinterpreted to be a propulsion command 910 intentionally given by the operator.

In certain examples, external stimulus applied to a portion of arm 212-designated may be interpreted as a basic forward propulsion command 910-1 or a basic backward propulsion command 910-2 that indicates only the propulsion direction and not the propulsion speed desired by the operator. In other examples, however, the external stimulus applied by an operator may be interpreted not only as a propulsion command 910 in a particular direction (forward or backward) along path 404, but also as a propulsion command 910 associated with a particular speed magnitude. Specifically, for example, system 100 may be configured, as part of the sensing of the external stimulus, to sense a magnitude of the sensed external stimulus, and to incorporate, as part of the interpreting of the sensed external stimulus, the magnitude into the propulsion command 910 so as to indicate both a direction and a speed magnitude that are to characterize the navigation of manipulator cart 202 along path 404. As such, when the operator applies more force to secondary control interface 900 (e.g., when arm 212-designated is configured to remain stiff rather than engage the breakaway clutch and the operator pulls or pushes harder on manipulator link 904 as determined by the motor force needed to match the exertion of the operator), manipulator cart 202 may navigate along path 404 at a higher rate of speed than when the operator applies less force.

In some examples, secondary control interface 900 may be configured to provide a consistent user experience for an operator who also has used or will use primary control interface 800. For example, the impedance to movement that an operator pushing or pulling on the handlebars of primary control interface 800 may be configured to be similar or the same as the impedance to movement that the operator may experience when pulling or pushing on a portion of arm 212-designated in secondary control interface 900.

Returning to FIG. 7, it will be understood that the primary control interface shown in standard navigation control mode 702 and bifurcated navigation control mode 704-1 may be implemented by primary control interface 800 (or another suitable primary control interface), while the secondary control interface shown in bifurcated navigation control mode 704-2 may be implemented by secondary control interface 900 (or another suitable secondary control interface). As such, the different navigation control modes 702 and 704 (and the corresponding control interfaces associated therewith) may be transitioned between in any suitable way and for any suitable reason, as illustrated by various transitions 706 in FIG. 7.

Before system 100 may operate in any navigation control mode 702 or 704 (i.e., before manipulator cart 202 can begin to move at all), manipulator cart 202 must first be determined to be navigable. Manipulator cart 202 may be navigable (i.e., able to be navigated, moved, driven, etc.) when the cart is powered on and the relevant control interface is operational, the powered drive is operational, no cannula or instrument is attached to any arm 212, parking feet of manipulator cart 202 are not deployed, and so forth. Even when manipulator cart 202 is navigable, however, additional factors may be examined by system 100 to determine whether either of bifurcated navigation control modes 704 are available for use. For example, system 100 may determine if a suitable path from an initial location to a target location (and, as applicable, from an initial orientation or configuration to a target orientation or configuration) can be defined. As described above, the entire path (e.g., path 404) may not need to be defined from the outset before manipulator cart 202 begins to traverse the path (i.e., because the path may be defined and updated dynamically as manipulator cart 202 is moving along the path). However, if sensors used for pathfinding are blocked or system 100 determines that no suitable path exists (e.g., because no path actually does exist, because a path cannot be found, because paths that are found are too complex or narrow, etc.), system 100 may determine (and indicate to the operator through visual, audible, haptic, or other suitable cues) that no bifurcated navigation control mode is currently available and that the standard navigation control mode will be required to navigate.

If system 100 determines that a bifurcated navigation control mode 704 is available for use, it may be desirable for manipulator cart 202 to navigate the entirety of path 404 in bifurcated navigation control modes 704 (e.g., starting with bifurcated navigation control mode 704-1 and later switching to bifurcated navigation control mode 704-2). However, in certain situations, particular conditions or events may cause bifurcated navigation control modes 704 to again become unavailable during the navigation, such that system 100 may switch from one of bifurcated navigation control modes 704 to standard navigation control mode 702 in order to allow operator control of both the steering and the propulsion of the manipulator cart using the primary control interface. Once any pathfinding issues are resolved (e.g., once obstacles have been cleared, once the target location is identified, once a valid path can be determined, etc.) and/or once an operator so indicates, system 100 may transition from standard navigation control mode 702 back to one of bifurcated navigation control modes 704.

In some examples, system 100 may receive, while in one of bifurcated navigation control modes 704, operator input resisting autonomous steering of the manipulator cart. For example, the operator input may be received at the primary control interface or the secondary control interface by the operator exerting a force on either the handlebars (of primary control interface 800) or arm 212-designated (of secondary control interface 900) that opposes the steering control that system 100 is performing. In other examples, operator input may not involve physically resisting the system steering control, but instead may involve the pressing of a button, the ceasing of pressing a button (e.g., a "dead-man's switch"), or the selection of another suitable user input mechanism by the operator. In response to any such operator input, system 100 may transition from directing the navigation along the path in the bifurcated navigation control mode 704 to directing the navigation along the path in standard navigation control mode 702. System 100 may also indicate to the operator (e.g., using a haptic rumble or any other feedback cue described herein) that the navigation control mode has been changed.

In other examples, the switching to standard navigation control mode 702 from the bifurcated navigation control mode 704 may be based on conditions other than explicit user input. For example, system 100 may identify a navigational condition associated with the navigation of manipulator cart 202 along path 404, and, based on the navigational condition, may transition (and indicate the transition to the operator) from directing the navigation along path 404 in one of bifurcated navigation control modes 704 to directing the navigation along path 404 in standard navigation control mode 702. The navigation condition identified may be any of various conditions and/or events that system 100 may detect. For example, the navigation condition may be that operating table 402 is detected to have moved from its prior location, thus necessitating a recalculating of location 406-target and path 404. In an example in which path 404 is being defined dynamically as manipulator cart 202 is navigating along the path, the navigation condition may be that path 404 becomes untenable, system 100 fails to find the next portion of path 404, line-of-sight to location 406-target is lost, sensors are blocked, or the like. In yet another example, detection of general motion of obstacles and objects within operating room 400 may cause system 100 to decrease a confidence level of a previously-defined path until it is determined that the path must be redefined. For instance, system 100 may measure the amount of entropy in the operating room, the level of activity in the operating room, or the like, and decide, based on that measurement, whether to proceed in a bifurcated navigation control mode 704 or to require navigation to proceed in standard navigation control mode 702 so that a human operator can determine how best to deal with the complexity.

Figure 10:
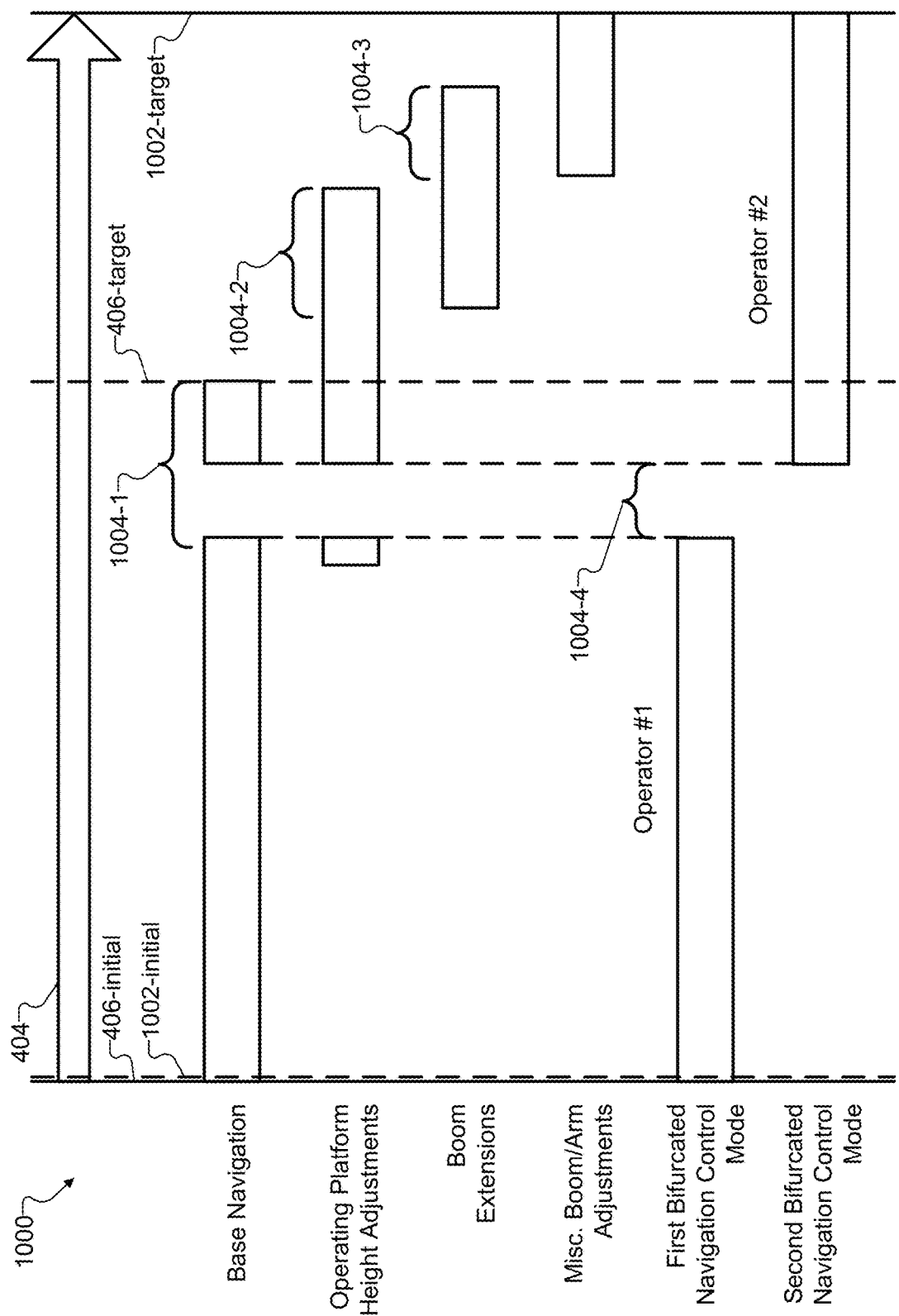
FIGS. 10 and 11 illustrate exemplary aspects of different exemplary navigations of a manipulator cart from an initial location and corresponding initial configuration to a target location and corresponding target configuration according to principles described herein.
Figure 11:
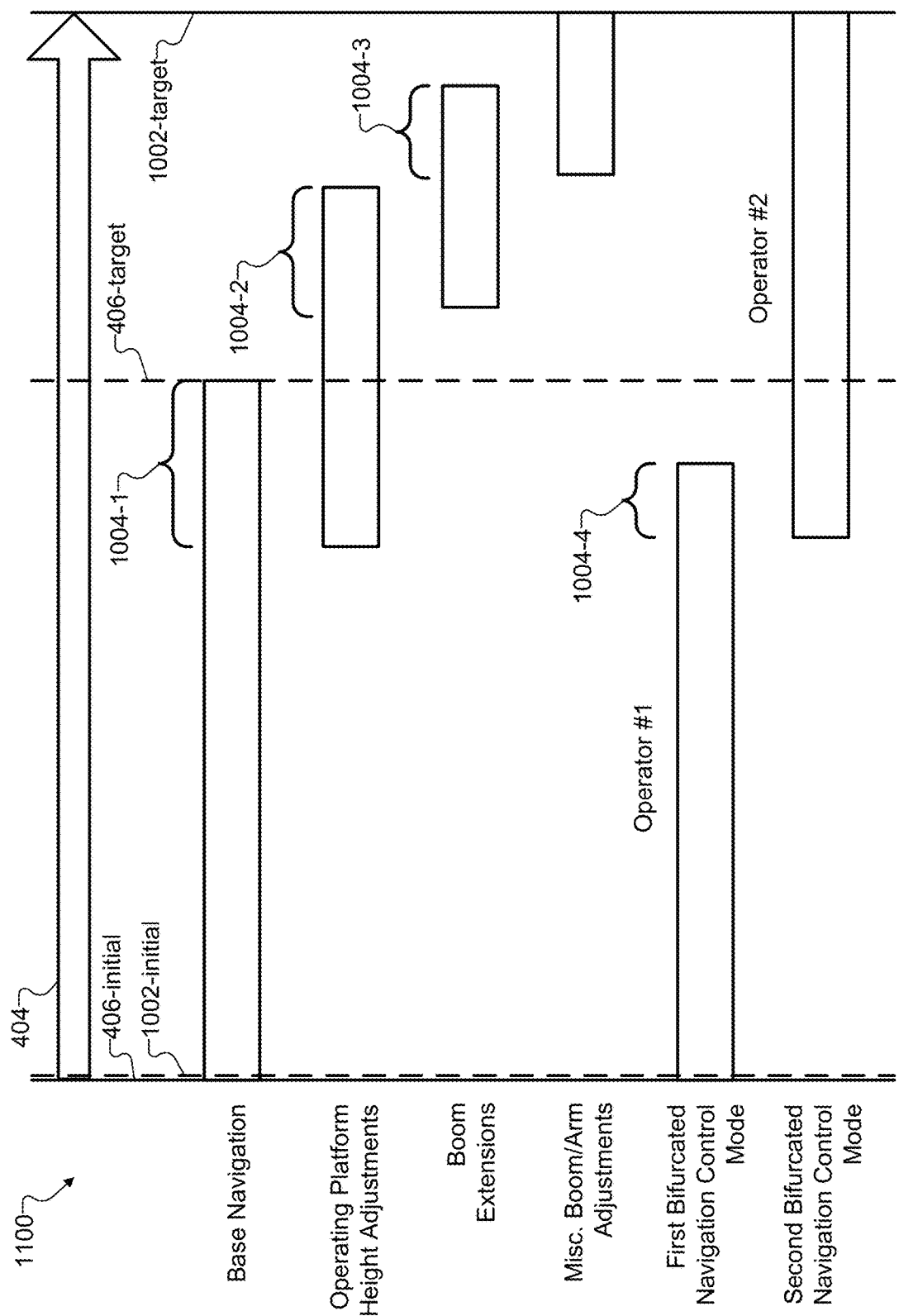

FIGS. 10 and 11 illustrate exemplary aspects of different exemplary navigations 1000 (in FIG. 10) and 1100 (in FIG. 11). Specifically, as shown, each of navigations 1000 and 1100 depict various navigational aspects as manipulator cart 202 navigates from location 406-initial (and a corresponding initial orientation and/or a corresponding initial configuration 1002-initial) to location 406-target (and a corresponding target orientation and/or a corresponding target configuration 1002-target) along path 404. The navigational aspects shown in FIGS. 10 and 11 include the "Base Navigation" (i.e., the movement of base 502 of manipulator cart 202 along path 404); the "Operating Platform Height Adjustments" (i.e., the raising and/or lowering of operating platform 504 in accordance with a configuration plan associated with path 404); the "Boom Extensions" (i.e., the extending and retracting of boom 506 in accordance with the configuration plan); any of various "Misc. Boom/Arm Adjustments"

(i.e., the pivoting, rotating, spreading, and other adjustments of boom 506 and/or arms 212 in accordance with the configuration plan); and whether navigation is being performed in a "First Bifurcated Navigation Control Mode" (e.g., bifurcated navigation control mode 704-1 using a primary control interface such as primary control interface 800) or in a "Second Bifurcated Navigation Control Mode" (e.g., bifurcated navigation control mode 704-2 using a secondary control interface such as secondary control interface 900).

As shown in FIGS. 10 and 11, path 404 may be considered to incorporate not only the navigation of base 502 along path 404, but also the configuration of various movable components of manipulator cart 202 described above. As such, in these examples, path 404 may be considered to have been completely traversed or navigated not when base 502 reaches location 406-target, but later when base 502 is positioned at location 406-target with the target configuration and/or each of the other movable components are properly configured in configuration 1002-target. It will be understood that, in other examples, path 404 may only extend until base 502 reaches location 406-target, and the orienting of the base 502 to the target orientation or the reconfiguring of the other movable components may not be integrated with the path navigation in this way.

Within FIGS. 10 and 11, various time periods 1004 (e.g., time periods 1004-1 through 1004-4) are called out to help illustrate how certain navigational aspects overlap or do not overlap as path 404 is navigated. Specifically, time period 1004-1 shows that operating platform 504 may be adjusted (e.g., lowered to avoid an overhead obstacle such as obstacle 412, raised to avoid arms 212 contacting operating table 402, etc.) during the same period of time that base 502 is being navigated along path 404. For example, operating platform 504 may begin to be raised as soon as manipulator cart passes under obstacle 412. While not shown in this example, it will similarly be understood that other movable components (e.g., boom 506, arms 212, etc.) may also be adjusted as base 502 is navigating along path 404 in certain situations and implementations.

Time period 1004-2 shows that, while operating platform 504 is being adjusted, boom 506 may also begin to extend. For example, the configuration plan may have boom 506 beginning to extend as soon as operating platform 504 has been raised enough so that boom 506 will not make contact with operating table 402 or a body located thereon as boom 506 is extended.

Time period 1004-3 shows that boom 506 may also begin to pivot and/or that arms 212 may be rotated, spread, and/or otherwise adjusted during a same period of time in which boom 506 is being extended. For example, as soon as the cannulas are visible using laser crosshairs disposed on each arm 212, rotations and other automatic adjustments may begin to occur to line up each arm 212 with a respective cannula on the body to which the arm will dock.

Time period 1004-4 is shown to be distinct in navigation 1000 (in FIG. 10) and navigation 1100 (in FIG. 11). Specifically, in navigation 1000, time period 1004-4 shows that there may be no overlap between the use of the first bifurcated navigation control mode and the use of the second bifurcated navigation control mode. Navigation 1000 thus represents an implementation or scenario in which the primary control interface (associated with the first bifurcated navigation control mode) and the secondary control interface (associated with the second bifurcated navigation control mode) are configured for non-concurrent use such that 1) the primary control interface is used to control the propulsion during a first time period, 2) the secondary control interface is used to control the propulsion during a second time period, and 3) the second time period is subsequent to and not overlapping with the first time period.

In this type of example illustrated by navigation 1000, an operator providing propulsion commands on each navigation control interface may be the same person in some situations. For instance, an operator (e.g. "Operator #1") may drive manipulator cart 202 using primary control interface 800 until location 406-intermediate is reached, and the same operator may then walk to the other side of manipulator cart 202 (e.g., possibly after scrubbing or finishing scrubbing to become sterilized) to provide propulsion commands using a secondary control interface such as secondary control interface 900. Conversely, in other situations, two different operators ("Operator #1" and "Operator #2") may each be associated with the navigation control in the different bifurcated navigation control modes. As shown, when no operator is exerting propulsion control during time period 1004-4, no navigation or other progression of movable components along path 404 may take place (i.e., the base navigation and adjustments to the operating platform height are shown to cease movement during this period).

In contrast, in navigation 1100 in FIG. 11, time period 1004-4 shows that there may be an overlap between the use of the first and the second bifurcated navigation control modes. Navigation 1100 thus represents an implementation or scenario in which the primary control interface and the secondary control interface are configured for concurrent use such that 1) a first operator ("Operator #1") performs the operator control of the propulsion of manipulator cart 202 using the primary control interface during a first time period, 2) a second operator distinct from the first operator ("Operator #2") performs the operator control of the propulsion of manipulator cart 202 using the secondary control interface during a second time period, and 3) the second time period overlaps with the first time period.

During time period 1004-4 in the example of navigation 1100, system 100 may be considered to concurrently be in both bifurcated navigation control modes 704, or may be considered to be in a third bifurcated navigation control mode (not explicitly illustrated in FIG. 7) in which control is performed using two different control interfaces (i.e., the primary and secondary control interfaces). In certain situations, the concurrent use of both primary and secondary control interfaces may not cause any problem because propulsion commands received by way of both control interfaces may be compatible, identical, or otherwise in agreement. For example, if the propulsion commands are generally in agreement (e.g., in the same direction and within a threshold amount of speed, etc.) an average propulsion command reflective of both compatible commands originating from both control interfaces may be used. In other situations, however, propulsion commands provided by these concurrent control interfaces may be different, incompatible, and otherwise not in agreement. In some examples, system 100 may take measures to avoid this situation (e.g., only presenting arm 212-designated for an operator to exert force on when no commands are being provided by way of the primary control interface, etc.). However, when such situations do arise, system 100 may prioritize one of the primary and secondary control interfaces over the other in order to resolve conflicting propulsion commands. This prioritization may be done in any suitable way as may serve a particular implementation.

For example, while the first time period overlaps with the second time period (i.e., during time period 1004-4 in FIG.

11), system 100 may prioritize the operator control of the propulsion of manipulator cart 202 using the primary control interface over the operator control of the propulsion of manipulator cart 202 using the secondary control interface. System 100 may prioritize the primary control interface in this way because the primary control interface is generally and traditionally the primary method of navigating manipulator cart 202, because primary control interface has more flexibility to allow the operator to exert control as needed (e.g., to transition to steering manipulator cart 202, to exert an emergency stop, etc.), or for any other suitable reason.

In other examples, while the first time period overlaps with the second time period (i.e., during time period 1004-4 in FIG. 11), system 100 may prioritize the operator control of the propulsion of manipulator cart 202 using the secondary control interface over the operator control of the propulsion of manipulator cart 202 using the primary control interface. System 100 may prioritize the secondary control interface in this way because the operator associated with the secondary control interface may be assumed to have a better vantage point on manipulator cart 202 as manipulator cart 202 makes a final approach to location 406-target or for any other suitable reason.

In still other examples, system 100 may identify a navigational condition associated with the navigation of manipulator cart 202 along path 404 and base priority on the navigational condition. Specifically, for example, based on the identified navigational condition, system 100 may prioritize (while the first time period overlaps with the second time period) the operator control of the propulsion of manipulator cart 202 using one of the primary and secondary control interfaces over the other of the primary and secondary control interfaces. The navigational condition may be a determination of which operator has better visibility of path 404 and the space around it for a particular segment of navigation 1100, where manipulator cart 202 is on path 404 (e.g., whether manipulator cart 202 has entered sterile are 408, etc.), a confidence level for how likely propulsion commands received via the secondary control interface are to be intentional and not misinterpreted, or any other navigational condition as may serve a particular implementation.

In either FIG. 10 or FIG. 11, once manipulator cart 202 reaches location 406-target (and the target orientation and/or configuration 1002-target as applicable), navigation of path 404 may be considered to be complete. At this point, the operation (e.g., the surgical procedure or other medical operation) may be performed. Thereafter, once the operation is complete, the same path 404 or a newly defined path may be used in a similar but reversed way as described herein to facilitate manipulator cart 202 in navigating back from location 406-target (and the target orientation and/or configuration 1002-target) to location 406-initial (and the initial orientation and/or configuration 1002-initial). In this case, the secondary control interface may be employed first to carefully back manipulator cart 202 away from the operating table and/or out of the sterile field, and the primary control interface may be employed thereafter to guide manipulator cart 202 back to a storage location or the like.

Figure 12:
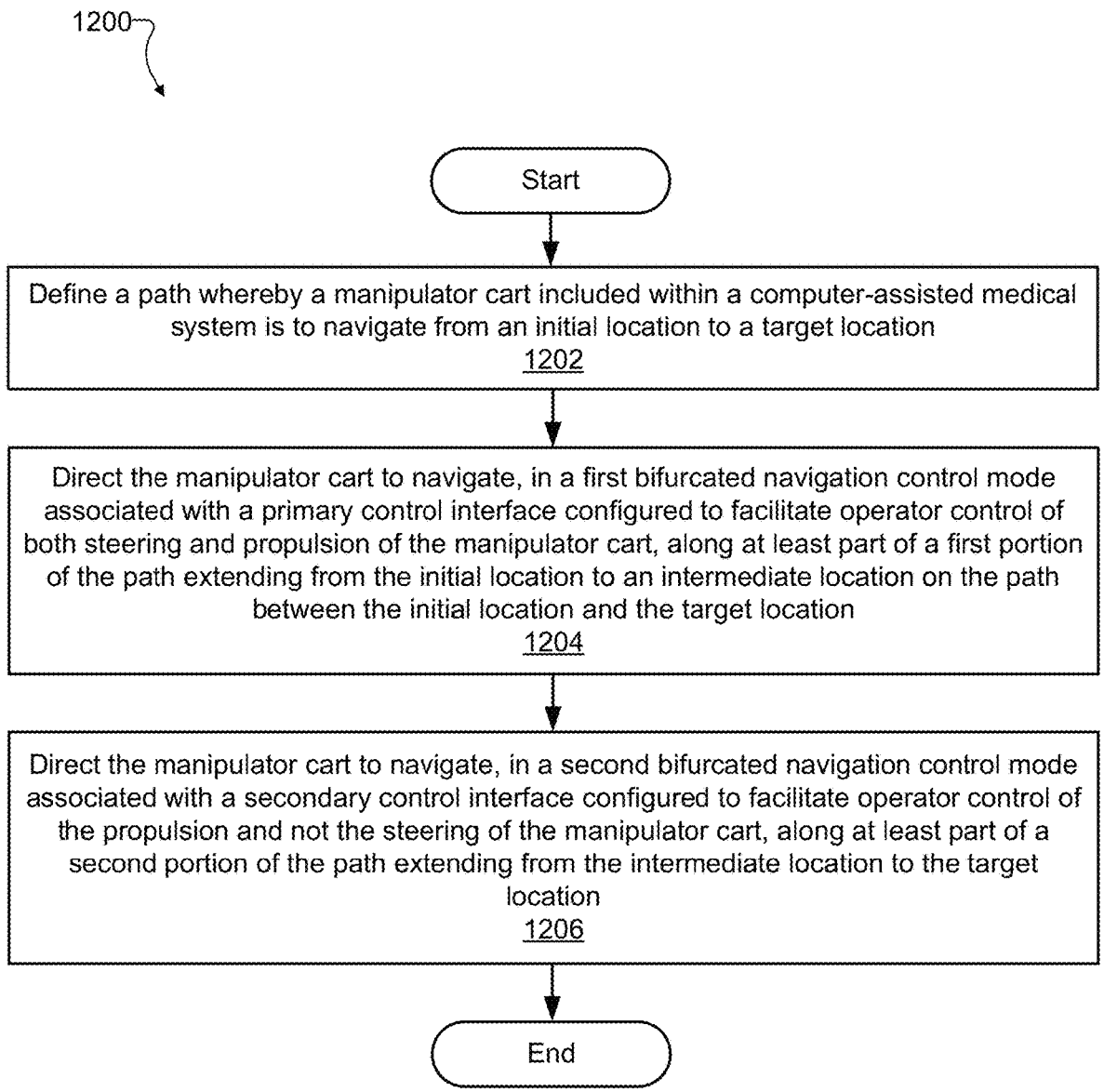
FIG. 12 illustrates an exemplary method for bifurcated navigation control of a manipulator cart included within a computer-assisted medical system according to principles described herein.

FIG. 12 illustrates an exemplary method 1200 for bifurcated navigation control of a manipulator cart included within a computer-assisted medical system. While FIG. 12 illustrates exemplary operations according to one embodiment, other embodiments may omit, add to, reorder, and/or modify any of the operations shown in FIG. 12. One or more of the operations shown in FIG. 12 may be performed by a bifurcated navigation control system such as system 100, any components included therein, and/or any implementation thereof.

In operation 1202, a bifurcated navigation control system may define a path whereby a manipulator cart included within a computer-assisted medical system is to navigate from an initial location to a target location. Operation 1202 may be performed in any of the ways described herein.

In operation 1204, the bifurcated navigation control system may direct the manipulator cart to navigate along at least part of a first portion of the path extending from the initial location to an intermediate location on the path between the initial location and the target location. For instance, the bifurcated navigation control system may direct the manipulator cart to navigate along at least part of this portion of the path in a first bifurcated navigation control mode in which the bifurcated navigation control system autonomously controls a steering of the manipulator cart while allowing operator control of a propulsion of the manipulator cart. In this first bifurcated navigation control mode, the operator control of the propulsion may be allowed using a primary control interface that is configured to facilitate operator control of both steering and propulsion of the manipulator cart. Operation 1204 may be performed in any of the ways described herein.

In operation 1206, the bifurcated navigation control system may direct the manipulator cart to navigate along at least part of a second portion of the path extending from the intermediate location to the target location. For example, the bifurcated navigation control system may direct the manipulator cart to navigate along at least part of this portion of the path in a second bifurcated navigation control mode in which the bifurcated navigation control system likewise autonomously controls the steering of the manipulator cart while allowing operator control of the propulsion of the manipulator cart. However, in this second bifurcated navigation control mode, the operator control of the propulsion may be allowed using a secondary control interface configured to facilitate operator control of the propulsion and not the steering of the manipulator cart. Operation 1206 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

In some examples, any of the systems and/or other components described herein may be implemented by a computing device including one or more processors, storage devices, input/output modules, communication interfaces, buses, infrastructures, and so forth. For instance, storage facility 102 of system 100 may be implemented by a storage device of the computing device, and processing facility 104 of system 100 may be implemented by one or more processors of the computing device. In other examples, the systems and/or other components described herein may be implemented by any suitable non-transitory computer-readable medium storing instructions that, when executed, direct a processor of such a computing device to perform methods and operations described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
direct a manipulator cart to navigate, in a first bifurcated navigation control mode, from an initial location to an intermediate location; and
direct the manipulator cart to navigate, in a second bifurcated navigation control mode, from the intermediate location to a target location;
wherein:
in the first bifurcated navigation control mode, the processor is configured to execute the instructions to autonomously control a steering of the manipulator cart while allowing operator control of a propulsion of the manipulator cart using a primary control interface configured to facilitate operator control of both steering and propulsion of the manipulator cart; and
in the second bifurcated navigation control mode, the processor is configured to autonomously control the steering of the manipulator cart while allowing operator control of the propulsion of the manipulator cart using a secondary control interface configured to facilitate operator control of the propulsion and not the steering of the manipulator cart.

2. The system of claim 1, wherein the processor is further configured to execute the instructions to define a path whereby the manipulator cart is to navigate from the initial location to the target location by way of the intermediate location.

3. The system of claim 2, wherein:
the initial location is associated with an initial orientation of the manipulator cart;
the target location is associated with a target orientation of the manipulator cart; and
the defining the path includes defining, with respect to the path, an orientation plan whereby the manipulator cart is reoriented from the initial orientation to the target orientation.

4. The system of claim 2, wherein:
the initial location is associated with an initial configuration of a movable component of the manipulator cart;
the target location is associated with a target configuration of the movable component of the manipulator cart; and
the defining the path includes defining, with respect to the path, a configuration plan whereby the movable component of the manipulator cart is to transform from the initial configuration to the target configuration.

5. The system of claim 2, wherein the defining the path comprises:
detecting an obstacle between the initial location and the target location;
determining a movability status or a risk factor of the obstacle; and
accounting for the movability status or the risk factor of the obstacle in the defining the path.

6. The system of claim 2, wherein the defining the path comprises:
detecting an obstacle between the initial location and the target location;
determining a risk factor associated with the obstacle; and
accounting for the risk factor of the obstacle in the defining the path.

7. The system of claim 2, wherein the processor is further configured to execute the instructions to:
direct, prior to the defining the path, the manipulator cart to be moved from a first location from which the target location is undetectable by a sensor of the manipulator cart to a second location from which the target location is detectable by the sensor;
determine, while the manipulator cart is at the second location, that the sensor detects the target location; and
designate, in response to the determining that the sensor detects the target location, the second location to be the initial location.

8. The system of claim 2, wherein the defining the path comprises:
defining a plurality of different paths whereby the manipulator cart could navigate from the initial location to the target location; and
selecting, from the plurality of different paths and based on input from an operator, the path whereby the manipulator cart is to navigate from the initial location to the target location.

9. The system of claim 2, wherein the processor is further configured to execute the instructions to update the path while the manipulator cart is navigating along the path.

10. The system of claim 2, further comprising at least one sensor selected from a group of sensors consisting of: a visual light image sensor, an infrared image sensor, or a depth sensor;
wherein the defining the path comprises:
receiving sensor data from the at least one sensor, and defining the path based on the received sensor data.

11. The system of claim 1, wherein the primary control interface includes a handlebar-based control interface integrated into the manipulator cart.

12. The system of claim 1, wherein:
the manipulator cart includes a set of one or more arms;
the secondary control interface is implemented using a portion of a designated arm of the set of one or more arms; and
the secondary control interface is configured to facilitate the operator control of the propulsion by:
sensing an external stimulus applied to the portion of the designated arm, and
in response to the sensed external stimulus meeting a set of criteria, interpreting the sensed external stimulus as a propulsion command.

13. The system of claim 12, wherein the set of criteria comprises a criterion based on a direction of the external stimulus.

14. The system of claim 13, wherein:
the external stimulus is interpreted as a forward propulsion command in response to the direction of the external stimulus being in a substantially forward direction; or
the external stimulus is interpreted as a backward propulsion command in response to the direction of the external stimulus being in a substantially backward direction; or
the external stimulus is not interpreted as the propulsion command in response to the direction of the of the external stimulus being substantially orthogonal to a path whereby the manipulator cart is to navigate from the initial location to the target location by way of the intermediate location.

15. The system of claim 12, wherein the set of criteria comprises:
a magnitude of the external stimulus being greater than a threshold magnitude; or
a frequency of the external stimulus being lower than a threshold frequency.

16. The system of claim 12, wherein:
the set of one or more arms includes a plurality of arms;
the designated arm is an only arm of the plurality of arms designated for implementing the secondary control interface; and
the designated arm is visually differentiated in the plurality of arms so as to be identifiable by an operator as the designated arm included in the secondary control interface.

17. The system of claim 12, wherein the secondary control interface is further configured to facilitate the operator control of the propulsion by:
as part of the sensing of the external stimulus, sensing a magnitude of the sensed external stimulus; and
as part of the interpreting of the sensed external stimulus, incorporating the magnitude into the propulsion command.

18. The system of claim 1, wherein:
the intermediate location is operator selected; or
the intermediate location is associated with a boundary of a sterile field, the sterile field including the target location while excluding the initial location.

19. A method comprising:
directing a manipulator cart to navigate, in a first bifurcated navigation control mode, from an initial location to an intermediate location; and
directing the manipulator cart to navigate, in a second bifurcated navigation control mode, from the intermediate location to a target location;
wherein:
in the first bifurcated navigation control mode, the method further comprises autonomously controlling a steering of the manipulator cart while allowing operator control of a propulsion of the manipulator cart using a primary control interface configured to facilitate operator control of both steering and propulsion of the manipulator cart; and
in the second bifurcated navigation control mode, the method further comprises autonomously controlling the steering of the manipulator cart while allowing operator control of the propulsion of the manipulator cart using a secondary control interface configured to facilitate operator control of the propulsion and not the steering of the manipulator cart.

20. A non-transitory computer-readable medium storing instructions that, when executed, direct a processor of a computing device to:
direct a manipulator cart to navigate, in a first bifurcated navigation control mode, from an initial location to an intermediate location; and
direct the manipulator cart to navigate, in a second bifurcated navigation control mode, from the intermediate location to a target location;
wherein:
in the first bifurcated navigation control mode, the processor autonomously controls a steering of the manipulator cart while allowing operator control of a propulsion of the manipulator cart using a primary control interface configured to facilitate operator control of both steering and propulsion of the manipulator cart; and
in the second bifurcated navigation control mode, the processor autonomously controls the steering of the manipulator cart while allowing operator control of the propulsion of the manipulator cart using a secondary control interface configured to facilitate operator control of the propulsion and not the steering of the manipulator cart.

* * * * *